United States Patent
Cohen et al.

(10) Patent No.: US 10,248,200 B2
(45) Date of Patent: Apr. 2, 2019

(54) WEARABLE DEVICES, WEARABLE ROBOTIC DEVICES, GLOVES, AND SYSTEMS, METHODS, AND COMPUTER PROGRAM PRODUCTS INTERACTING WITH THE SAME

(71) Applicant: Drexel University, Philadelphia, PA (US)

(72) Inventors: Andrew Cohen, Philadelphia, PA (US); Genevieve Dion, Philadelphia, PA (US); Mark Winter, Wynnewood, PA (US); Eric Wait, Ardmore, PA (US); Michael Koerner, Lansdale, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 15/123,236

(22) PCT Filed: Feb. 27, 2015

(86) PCT No.: PCT/US2015/018192
§ 371 (c)(1),
(2) Date: Sep. 1, 2016

(87) PCT Pub. No.: WO2015/134336
PCT Pub. Date: Sep. 11, 2015

(65) Prior Publication Data
US 2017/0168565 A1    Jun. 15, 2017

Related U.S. Application Data

(60) Provisional application No. 62/117,179, filed on Feb. 17, 2015, provisional application No. 61/946,820, filed on Mar. 2, 2014.

(51) Int. Cl.
*A61B 5/00*   (2006.01)
*A61B 5/22*   (2006.01)
(Continued)

(52) U.S. Cl.
CPC ............ *G06F 3/014* (2013.01); *A61B 5/0022* (2013.01); *A61B 5/225* (2013.01); *A61B 5/6806* (2013.01);
(Continued)

(58) Field of Classification Search
CPC .............................. G06F 3/014; A61H 1/0288
See application file for complete search history.

(56) References Cited

U.S. PATENT DOCUMENTS 4,084,267 A    4/1978  Ladina
4,861,645 A    8/1989  Standing
(Continued)

FOREIGN PATENT DOCUMENTS

EP    2624238 A1    8/2013

OTHER PUBLICATIONS

Brown, et al, "The exoskeleton glove for control of paralyzed hands" 1993, vol. 1, pp. 642-647, IEEE International Conference on Robotics and Automation.
(Continued)

*Primary Examiner* — Laurence J Lee
(74) *Attorney, Agent, or Firm* — Schott, P.C.

(57) ABSTRACT

One aspect of the invention provides a wearable device including: at least one compliant region adapted and configured to be placed over a joint of a subject and at least two flexible but less compliant regions coupled to opposite ends of the compliant region. Another aspect of the invention provides a wearable robotic device including a wearable device as described herein and at least one actuator adapted and configured to move the flexible but less compliant regions relative to each other.

18 Claims, 20 Drawing Sheets

(51) Int. Cl.
  *A61F 2/58*    (2006.01)
  *A61F 5/01*    (2006.01)
  *A61H 1/02*    (2006.01)
  *G06F 3/01*    (2006.01)
  *B25J 13/02*    (2006.01)

(52) U.S. Cl.
  CPC ............ *A61F 2/583* (2013.01); *A61F 5/0102* (2013.01); *A61F 5/013* (2013.01); *A61H 1/0288* (2013.01); *B25J 13/025* (2013.01); *G06F 3/016* (2013.01)

(56) References Cited

U.S. PATENT DOCUMENTS

| | | | |
|---|---|---|---|
| 7,967,679 B2 | 6/2011 | Ombrellaro et al. | |
| 8,029,414 B2 | 10/2011 | Ingvast et al. | |
| 8,362,882 B2 | 1/2013 | Heubel et al. | |
| 9,375,382 B2* | 6/2016 | Fausti | A61H 1/0285 |
| 2006/0094989 A1* | 5/2006 | Scott | A61F 2/54 601/5 |
| 2007/0226873 A1* | 10/2007 | Mattesky | A41D 19/0006 2/159 |
| 2011/0105978 A1* | 5/2011 | Hou | B32B 5/04 602/75 |
| 2012/0204322 A1* | 8/2012 | Fukushima | D01D 5/247 2/167 |
| 2013/0072829 A1* | 3/2013 | Fausti | A61H 1/0285 601/40 |
| 2013/0226350 A1* | 8/2013 | Bergelin | B25J 9/0006 700/275 |
| 2013/0291282 A1* | 11/2013 | Anstey | A41D 19/015 2/161.7 |
| 2014/0039367 A1* | 2/2014 | Boraas | A61F 5/01 602/7 |

OTHER PUBLICATIONS

Favetto, et al, "Embedding an Exoskeleton Hand in the Astronaut's EVA Glove: Feasibility and Ideas" 2012, vol. 1 No. 4, pp. 68-76, International Journal of Aerospace Sciences, Italy.

Martinez, et al, "A Power-assisted Exoskeleton Optimized for Pinching and Grasping Motions" Mar. 2010, IEE Bioengineering Conference.

Paleari, et al, "Hexec: A Hand Exoskeleton Designed to be Embedded in the Astronaut's Eva Glove" 2012, Center of Space Human Robotics.

PCT Preliminary Report on Patentability and Written Opinion of the International Searching Authority, PCT/US2015/018192, filing date Feb. 27, 2015.

* cited by examiner

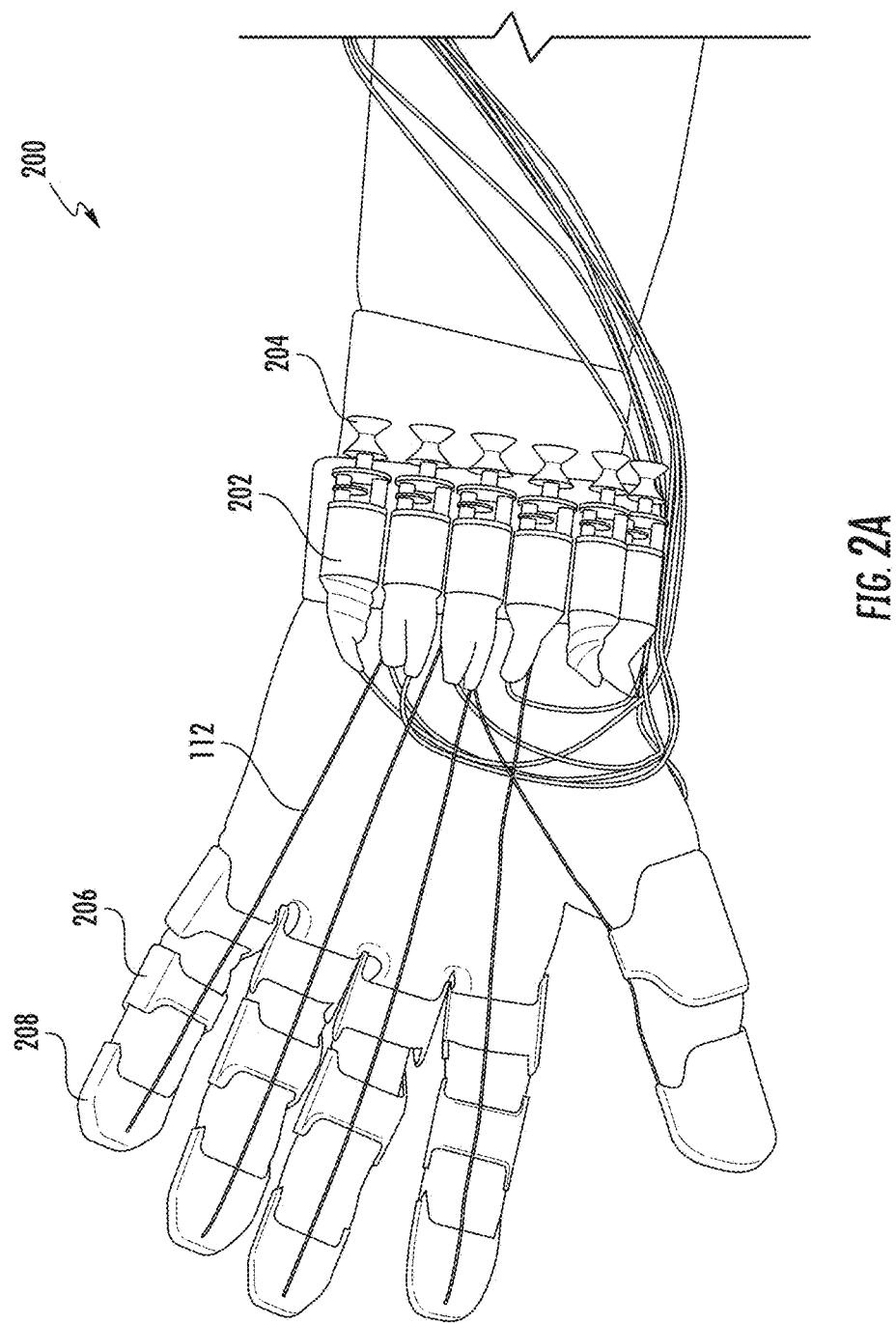

WEARABLE DEVICES, WEARABLE ROBOTIC DEVICES, GLOVES, AND SYSTEMS, METHODS, AND COMPUTER PROGRAM PRODUCTS INTERACTING WITH THE SAME

STATEMENT REGARDING GOVERNMENT SUPPORT

This invention was made with government support under Grant No. R01AG040080 from the National Institutes of Health. The U.S. Government has certain rights in this invention.

BACKGROUND

Despite the increasing availability of three-dimensional (3-D) images in a variety of fields such as medicine, science, and gaming, 3-D images remain challenging for users to comprehend, manipulate, and interact with. Moreover, current wearable robotics devices have large form factors that limit their suitability for real-world use.

SUMMARY OF THE INVENTION

A wearable device includes at least one compliant region adapted and configured to be placed over a joint of a subject and at least two flexible but less compliant regions coupled to opposite ends of the compliant region.

The at least one compliant regions may include a textile. The at least one compliant region may include a textile including one or more fibers such as natural fibers, cotton, wool, silk, hemp, flax, animal hair, jute, modal, cellulose, bamboo, piña, ramie, nettles, milkweed, seaweed, metals, manufactured fibers, azlon, acetate, triacetate, viscose, lyocell, glass, graphite carbon, carbon fiber, carbon nanotube, liquid crystal, ceramics, polyesters, aramids, para-aramids, meta-aramids, aromatic polyesters, rayon, acrylics, modacrylics, polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nytril, elastoester, nylon, spandex/elastane, olefins, biosynthetic polymers, and blends of the same.

The at least one compliant regions may include an elastomer. The at least one compliant regions may be capable of elongation between about 160% and about 180%.

The flexible but less compliant regions may include textiles. The at least one flexible but less compliant regions may also include a textile including one or more fibers including natural fibers, cotton, wool, silk, hemp, flax, animal hair, jute, modal, cellulose, bamboo, piña, ramie, nettles, milkweed, seaweed, metals, manufactured fibers, azlon, acetate, triacetate, viscose, lyocell, glass, graphite carbon, carbon fiber, carbon nanotube, liquid crystal, ceramics, polyesters, aramids, para-aramids, meta-aramids, aromatic polyesters, rayon, acrylics, modacrylics, polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nytril, elastoester, nylon, spandex/elastane, olefins, biosynthetic polymers, and blends of the same. The flexible but less compliant regions may include an elastomer. The at least one flexible but less compliant regions may be capable of elongation between about 91% and about 111%.

A wearable robotic device may include a wearable device with at least one compliant region adapted and configured to be placed over a joint of a subject and at least two flexible but less compliant regions coupled to opposite ends of the compliant region; and at least one actuator adapted and configured to move the flexible but less compliant regions relative to each other.

The at least one actuator may facilitate a movement of the joint including flexion, extension, abduction, and adduction. The actuator may be a tendon. The actuator may include a piston, a DC motor, a stepper motor, a linear actuator, an electroactive polymer (EAP), and a pneumatic muscle.

The joint may include a hand joint, an elbow joint, a wrist joint, a shoulder joint, a sternoclavicular joint, a vertebral joint, a temporomandibular joint, a sacroiliac joint, a hip joint, a knee joint, an ankle joint, and a foot joint.

The subject may be a human, canine, or other animal.

The wearable device may be a glove. The glove may include a plurality of fingers and each finger may be associated with at least one actuator.

The wearable robotic device may further include one or more force sensors adapted and configured to detect movement by the subject. The wearable robotic device may further include a pair of force sensors positioned on opposite sides of a subject's bone.

The wearable robotic device may further include one or more vibrotactile devices adapted and configured to provide feedback to the subject.

A glove may include at least one sleeve adapted and configured to receive at least one finger of a subject and at least one actuator. At least one of the sleeves may include a compliant region adapted and configured to be placed over a metacarpophalangeal or interphalangeal joint of a subject; two less compliant regions coupled to opposite ends of the compliant region; and at least one pair of force sensors positioned on opposite sides of a distal tip of the sleeve. The at least one actuator may be adapted and configured to move the less compliant regions relative to each other in response to forces sensed by the force sensors.

The glove may further include at least one actuator for each of the subject's fingers.

The glove may further include at least two actuators for each of the subject's fingers. The at least two actuators for each of the subject's fingers may be adapted and configured to cause opposing movements of the subject's fingers. The opposing movements may include flexion and extension. The opposing movements may include abduction and adduction.

The compliant region and the less compliant regions may comprise textiles of varying compliance.

The at least one actuator may include at least one tendon. The at least one tendon may be coupled to a motor and a winch.

A related system may include a glove, a sensor, and a tangible, non-transitory computer program product. The glove may include at least one sleeve and at least one actuator. The at least one sleeve may be adapted and configured to receive at least one finger of a subject. At least one of the sleeves includes: a compliant region adapted and configured to be placed over a metacarpophalangeal or interphalangeal joint of a subject; and two less compliant regions coupled to opposite ends of the compliant region.

The at least one actuator may be adapted and configured to move the less compliant regions relative to each other. The sensor is adapted and configured to detect a position of the glove within a three-dimensional space. The tangible, non-transitory computer program product may be programmed to: map the position of the at least one of the subject's fingers with respect to one or more computer-generated structures; and control the at least one actuator to inhibit movement of at least one of the subject's fingers when the position of the at least one finger is adjacent to a boundary of one of the computer-generated structures.

This aspect of the invention may have a variety of embodiments. The computer program product may be further programmed to display the position of the at least one of the subject's fingers and the one or more computer-generated structures on a display device.

The computer program product may be further programmed to modulate inhibition of movement based on a defined compliance of the one or more computer-generated structures. The defined compliance may be user-definable.

The computer-generated structures may represent real-world structures. The real-world structures may be anatomical structures. The computer-generated structures may be derived from imaging data produced using one or more techniques such as magnetic resonance imaging (MRI), ultrasonography, positron emission topography (PET), computed tomography (CT), diffuse optical tomography, elastography, electrical impedance tomography, 3-D microscopy, and 3-D confocal laser microscopy.

A related method may include loading one or more computer-generated structures; receiving information regarding at least one position of a subject's body; mapping the at least one position relative to the one or more computer-generated structures; and transmitting instructions to a wearable hardware device to inhibit movement of at least one portion of the subject's body when the portion of the subject's body is adjacent to a boundary of one of the computer-generated structures.

A tangible and non-transitory computer program product may comprise instructions for performing a method including: loading one or more computer-generated structures; receiving information regarding at least one position of a subject's body; mapping the at least one position relative to the one or more computer-generated structures; and transmitting instructions to a wearable hardware device to inhibit movement of at least one portion of the subject's body when the portion of the subject's body is adjacent to a boundary of one of the computer-generated structures.

BRIEF DESCRIPTION OF THE DRAWINGS

FIGS. 2A and 2B show an alternate glove.

DEFINITIONS

Figure 1A:
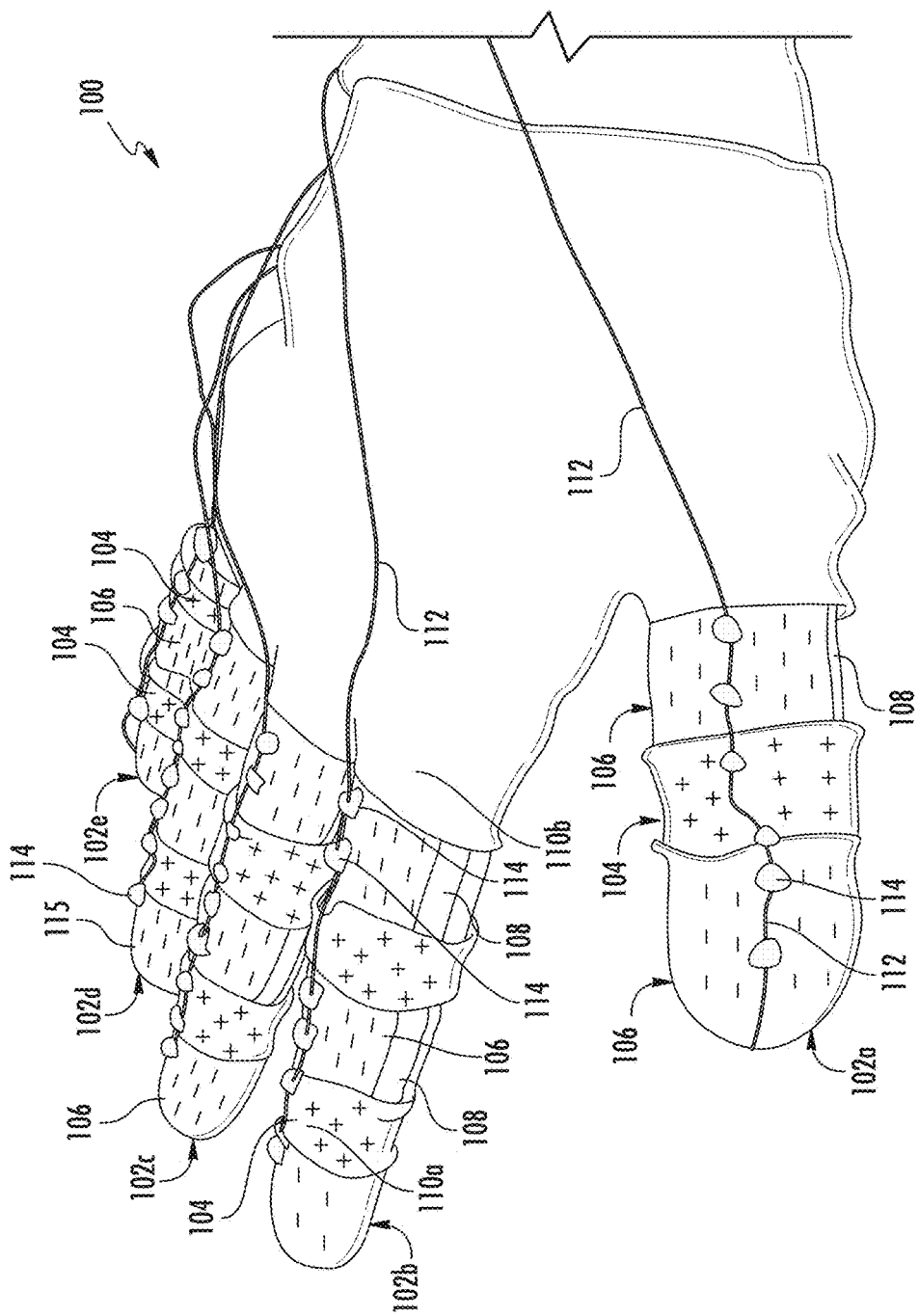
FIGS. 1A and 1B show a glove.

As used in the specification and claims, the singular form "a," "an," and "the" include plural references unless the context clearly dictates otherwise.

Unless specifically stated or obvious from context, as used herein, the term "about" is understood as within a range of normal tolerance in the art, for example within 2 standard deviations of the mean. About may be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

As used in the specification and claims, the terms "comprises," "comprising," "containing," "having," and the like may have the meaning ascribed to them in U.S. patent law and may mean "includes," "including," and the like.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

Unless specifically stated or obvious from context, as used herein, the term "or" is understood to be inclusive.

DESCRIPTION OF THE INVENTION

Wearable devices, wearable robotic devices, and systems methods, and computer-program products using the same may be used not only by human subjects, but also by animals such as canines. For example, the apparatus, method, and system may be used by soldiers or law enforcement officers, as well as service dogs.

An active haptic exoskeleton device may be used, for example, as: a device used for haptic interaction with 5-D stem cell data, a wearable assistive and rehabilitative device for strength augmentation of the hand, and a commercial device for virtual reality and perception augmentation (gaming). Aspects of the glove augment forces as well as delivering textural feedback to each individual fingertip.

Each finger may be controlled by two actuator cables that mimic the flexor and extensor tendons of the hand. A vibrotactile motor may be located at each fingertip and may be used to simulate the texture of a virtual surface. The artificial tendons run through pathways knitted into the glove and attach to the actuators mounted on the wrist cuff. The two actuators for each finger work in unison, receiving force feedback data from two sensors mounted in each fingertip, actively adapting to the natural motion of the hand. The glove may then augment this natural motion to simulate forces on the hand. In conjunction with the vibrotactile stimulus, this creates an immersive haptic experience unlike any commercial or academic system. The same glove may provide remote rehabilitation as well as strength augmentation to patients, revolutionizing the field of rehabilitative and assistive robotics.

An exoskeletal glove may include outer-layer, a sensor glove under-layer, a tendon-driving actuator cuff, and a control array.

The knitted semi-rigid exoskeletal outer layer may combine the concepts of rigid and soft exoskeletons, gaining the benefits of each. The layer may be knitted and steamed using techniques that ensure the tendon pathways are aligned and kept open. It provides a near frictionless guide for the artificial tendons that allow for near-lossless force transmittance to the fingertip. The actuator tendon pathways mimic the flexor and extensor tendons of the hand and seamlessly mimics and drives both sets of tendons with a hand-mounted actuating system. Current systems use large bulky exoskeletons that are impractical for most use cases and restrict the natural motion of the hand and are more restrictive than the glove described herein.

The knitted sensor under-layer may hold the fingertip FSRs (force sensing resistors) in place as well as neatly guides the wires necessary for communication with the control array (10 per finger, 50 total). Conductive yarn may be used to create the necessary conductive pathways, allowing the sensor glove to be thin and non-obstructive to the hand's natural motion. All wires may be fed into a pin-out port on the wrist so the glove may easily be disconnected from the control array for mobility purposes. No current technologies use a bi-layer approach or conductive yarn as a signal transmission method. The placement of the force sensors in the fingertip of the system is also unique. The sensors are in constant contact with both the fingertip and exoskeletal layer, allowing for instantaneous and accurate localized force readings.

The wrist cuff with tendon actuator array may be also include a method for driving the exoskeleton. This is the first system to place ten independently controlled tendon actuators on the hand of the user, as well as the first system to actively articulate each finger independently using a mimicked flexor and extensor tendon. Previous technologies drive the exoskeleton using off-arm methods that introduce friction and lag into the force transmission system. By placing the actuators as close to the fingertip as possible, most traditional sources of friction and cable drag are eliminated. Having on-hand actuators also allows the exoskeleton to be a standalone system, requiring no tether to a bulky driving mechanism. This key factor allows the system to be a wearable robotic grip assistive device or constant-contact rehabilitative system.

The semi-rigid knitted exo-skin may use the SHIMA SEIKI® WHOLEGARMENT® knitting machine model SWG041N available from Shima Seiki Manufacturing, Ltd. of Wakayama, Japan. The skin may be designed using Shima's proprietary software, creating a "program" that may be read by any machine to produce the desired product. Each finger may include three semi-rigid segments that fit over the proximal, middle, and distal phalanges. Stretchable segments connect these semi-rigid pieces, allowing for a full range of motion of the DIP (distal interphalangeal), PIP (proximal interphalangeal), and MCP (metacarpophalangeal) joints. Knitted padding may be incorporated into the top of each stretchable segment to prevent wear on the knuckle from the cable. Actuated flexor and extensor cables run along the top and bottom of each finger, each attaching to the tip of the distal phalange. The tendons may run through knitted guides that are oriented during the steaming process. After the glove is knitted, it may be placed on a porcelain hand; rods are forced through the tendon guides, and the glove is steamed. The steaming process causes the glue yarn in the semi-rigid segments to harden, taking the shape of the porcelain finger as well as fixing the cable guides in the proper orientation.

The thin sensor underlayer may include of ten force sensing resistors (FSRs), one on top and bottom of each distal phalange. The sensors may be secured to the under glove, and conductive yarn may be used to create the necessary wiring pathway to the wrist cuff of the glove. The yarn follows a specific zigzag pathway delineated by pointelle holes incorporated into the knitted design. The twenty wires running from the fingertip FSRs as well as the ten wires running from the fingertip vibro-tactile motors may attach to a pin-out port on the wrist cuff for ease of coupling to a control device (e.g., an ARDUINO® microcontroller).

Base Layer for Wearable Robotic Devices

Referring now to FIG. 1A, a glove 100 includes a plurality of fingers 102 that are individual fingers 102a, 102b, 102c, 102d, and 102e. As labeled in the context of thumb 102a, each of the fingers 102 may include one or more compliant regions 104 and flexible, but less compliant regions 106, both of which have open cylindrical shapes that encircle the finger 102 joint. The compliant regions 104 may be posited for placement over a joint of a subject's hand. Similarly, the flexible, but less compliant regions 106 may couple to the compliant regions 104. In such a manner, the flexible, but less compliant regions 106 align with the subject's bones in order to mimic the subject's anatomy and/or provide support.

The glove 100 may be made from a variety of materials such as textiles and elastomers. Textiles advantageously provide excellent compliance and breathability. Suitable textiles may be made from a variety of natural and synthetic fibers such as natural fibers, cotton, wool, silk, hemp, flax, animal hair, jute, modal, cellulose, bamboo, piña, ramie, nettles, milkweed, seaweed, metals, manufactured fibers, azlon, acetate, triacetate, viscose, lyocell, glass, graphite carbon, carbon fiber, carbon nanotube, liquid crystal, ceramics, polyesters, aramids, para-aramids, meta-aramids, aromatic polyesters, rayon, acrylics, modacrylics, polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nytril, elastoester, nylon, spandex/elastane, olefins, biosynthetic polymers, and blends of the same. Suitable aramids, para-aramids, and meta-aramids are sold under the KEVLAR® and NOMEX® brands by E. I. du Pont de Nemours and Company of Wilmington, Del., under the TECHNORA® brand by Teijin Limited of Osaka, Japan, and under the TWARON® brand by Teijin Aramid B.V. of Arnhem, The Netherlands. Suitable aromatic polyesters are available under the VECTRAN® and VECTRAN® EX brands from Kuraray America, Inc. of Fort Mill, S.C.

To achieve compliance difference between complaint regions 104 and flexible, but less compliant regions 106, the compliant regions 104 may be textiles having thinner fibers than flexible, but less compliant regions 106. In another example, flexible, but less compliant regions 106 may have a denser and/or tighter weave, knit, or the like. In yet another example, a treatment applied to the flexible, but less compliant regions 106 may decrease their compliance as discussed below.

Flexible but less compliant regions 106 may be treated by applying energy to fuse, melt, cross-link, or otherwise increase the rigidity of the textiles, especially synthetic textiles. For example, infrared, ultraviolet, RF, microwave, ultrasound, or other forms of energy may be applied to the textile. For example, glove 100 may be placed over a hand-shaped mold including energy-supplying regions corresponding to the desired locations of flexible, but less compliant regions 106. For example, energy-supplying regions may include a plurality of vents adapted and configured to release hot air or steam into flexible, but less compliant regions 106.

Figure 1B:
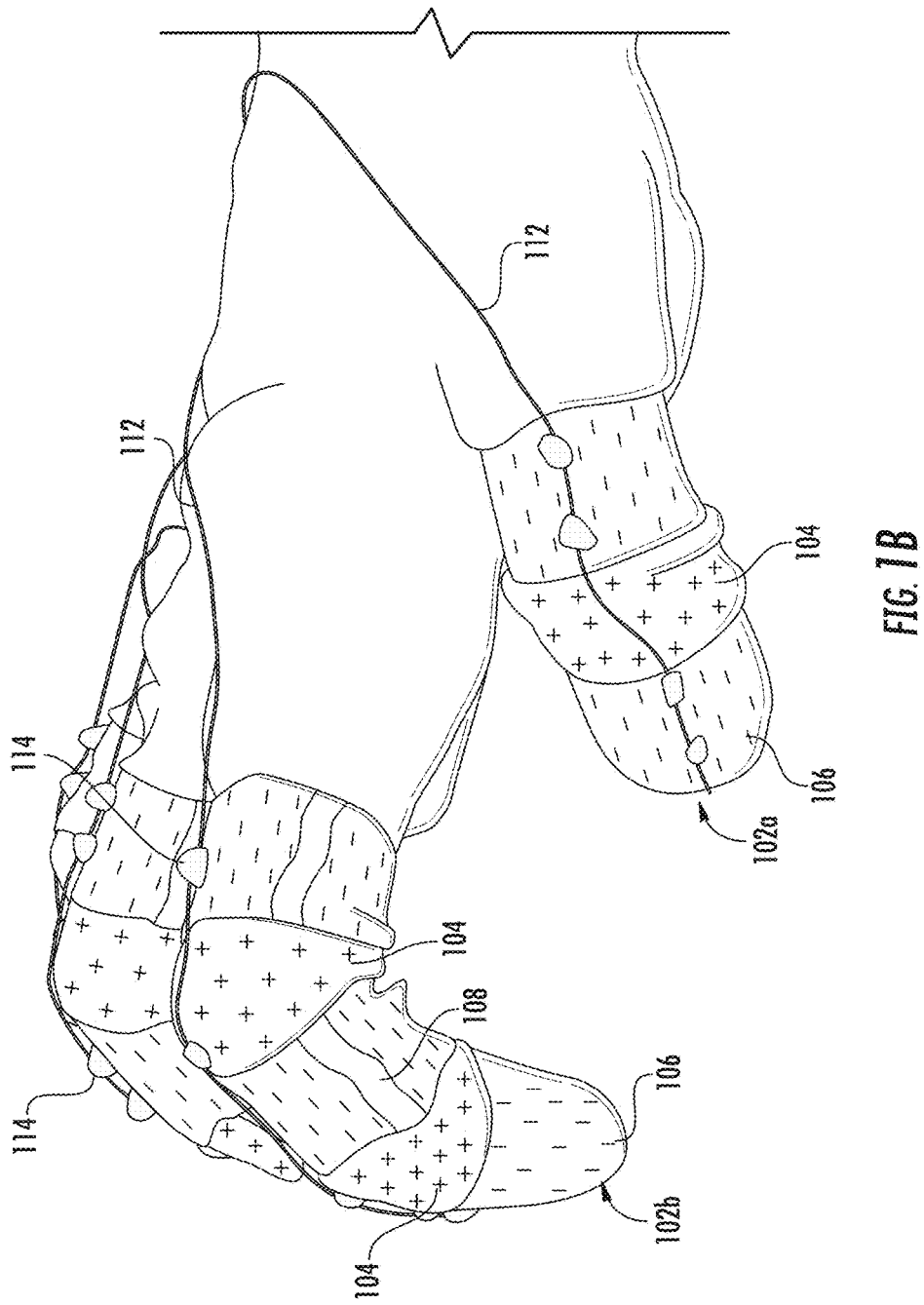

As seen in FIG. 1B, compliant regions 104 are sufficiently compliant or flexible in order to permit normal joint movement as though the subject is not wearing glove 100 or other base layer. For example, the individual yarns within a textile may be capable of elongation of between about 110% and about 130% and the textile may be capable of elongation between about 160% and about 180%.

Flexible, but less compliant regions 106 may be sufficiently compliant or flexible to stretch in order to permit an adjacent joint (an interphalangeal joint) to pass through the flexible, but less compliant regions 106 before compressing slightly against the adjacent bones. For example, the textile may have an elongation between about 95% and about 115%, which may be further reduced to between about 91% and about 111% by steam treatment. Flexible, but less compliant regions 106 may include one or more elastic regions 108 that permit stretching of the flexible, but less compliant regions 106 when passing over joints. Suitable elastic materials include spandex, which is available, for example, under the LYCRA® trademark from Invista North America S.A.R.L. of Wichita, Kans.

Textiles for compliant regions 104 and flexible, but less compliant regions 106 may be formed using a variety of manual or automated means. For example, textiles may be formed using an industrial knitting machine. Knitting is the intermeshing of yarns into loops resulting in fabrics. In particular, knitting is the process of creating fabric with yarns by forming a series of interconnected loops. For example, textiles may be formed using an industrial flatbed knitting machine. Three-dimensional knitted shapes may be made using various loop configuration (knit stitches) such as knit and purl, tuck, miss, and the like and/or various shaping techniques such as flechage, bindoff, tubular half gauge and the like. In one embodiment, plissage is used under finger segments to facilitate bending and kinematic mimicry and ensure that fabric does not pile up under joints when bending fingers. All techniques may be used individually or in combinations with one another within the same structure.

The glove 100 may include padding 110a, 110b in regions where tendons 112 (discussed below) pass over an articulation point of the subject's anatomy and/or where one or more actuators and/or other electromechanical elements are located. Padding 110 may include adding knitting, layers, or compressible materials (e.g., foams). One or more layers of the glove may fold over to cover actuators and/or other electromechanical elements.

Although a glove 100 is depicted, the base layer may be applied to any anatomical joint including, but not limited to, a hand joint, an elbow joint, a wrist joint, a shoulder joint, a sternoclavicular joint, a vertebral joint, a temporomandibular joint, a sacroiliac joint, a hip joint, a knee joint, an ankle joint, a foot joint, and the like.

Wearable Robotic Devices

Still referring to FIG. 1A, the glove 100 provides a wearable robotic device that combines glove 100 or other base layer with actuators. Actuators may be adapted and configured to move the flexible, but less compliant regions 106 relative to each other. For example, actuators may facilitate flexion, extension, abduction, or adduction of a joint. Such movement may be achieved through applying tension or compression to one side of the joint.

Still referring to FIG. 1A, a plurality of tendons 112 apply tension to one or more sides of bone. Tendons 112 may be fabricated from a variety of materials such as wires, cables, strings, ropes, twine, and/or the fibers discussed herein in the context of textiles. Tendons 112 may be woven through the base material of the glove and may be optionally sheathed. As shown in FIG. 1, a plurality of knitted tendon pathways 114 shown attached to the glove 100 via attachment points 115 may sit above the glove surface and allow tendon 112 to run along the outside of glove 100.

Figure 2B:
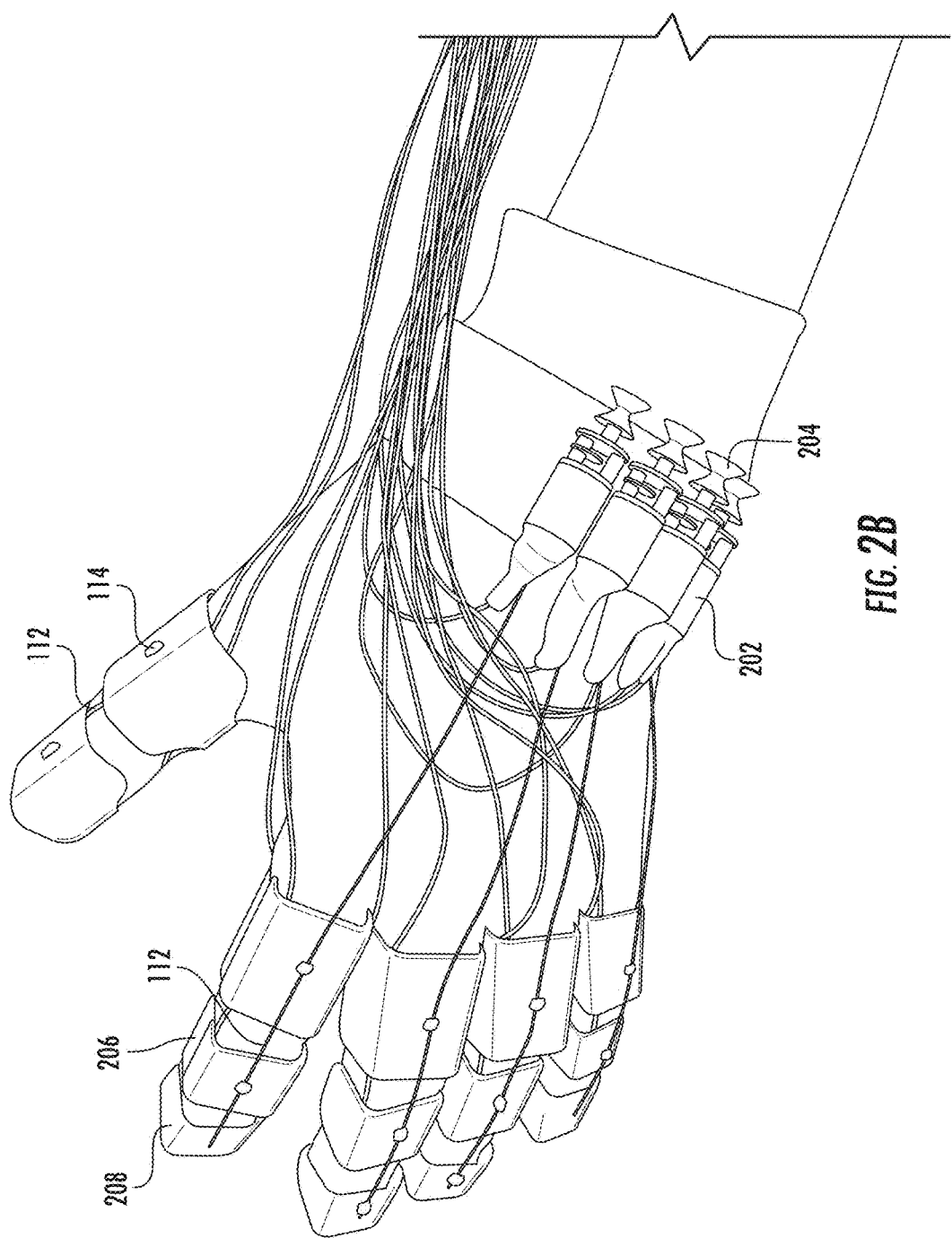

Referring now to FIG. 2A and FIG. 2B, where FIG. 2A shows the palm side of the hand and FIG. 2B shows the back of the hand, tendons 112 may be manipulated by one or more motors 202 such as a DC motor, a stepper motor, a servomotor, and the like. Motors 202 may apply tension to tendons 112 in order cause the desired motion of the underlying joint. For example, motor 202 may turn a winch 204 to draw in or release tendon 112.

A variety of other actuators may be used such as linear actuators, electroactive polymers (EAPs), pneumatic muscles, and the like.

Although glove 200 includes a plurality of rigid members 206, 208 fabricated from molded plastic, the principles discussed herein apply with equal force.

The dorsal side of glove 200 is shown in FIG. 2B. As may be seen, parallel structures are present on the dorsal side in order to facilitate extension of one or more fingers.

Opposing Force Sensors

Figure 3A:
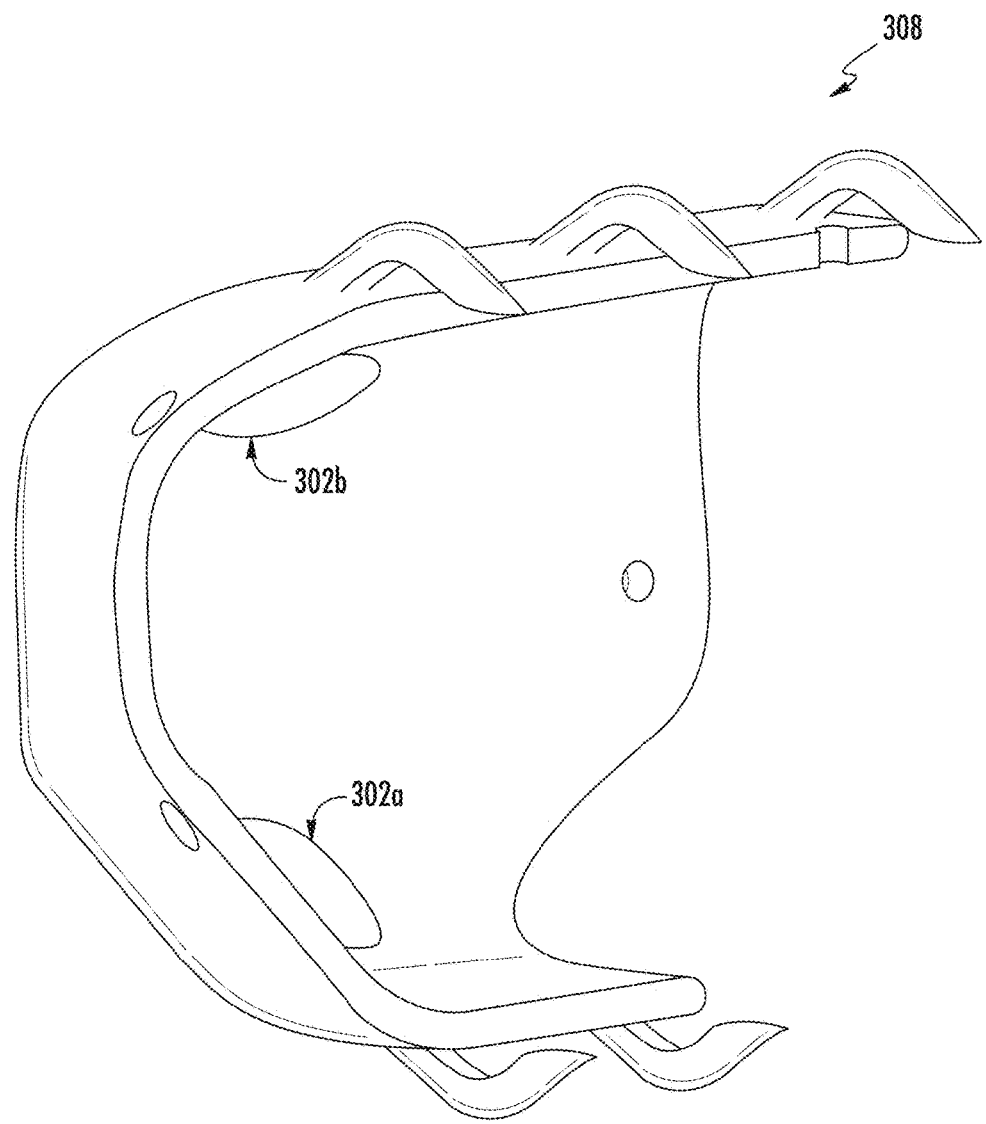
FIG. 3A depicts positioning of force sensors on opposite sides of a subject's finger tip.

Referring now to FIG. 3A, rigid members 308 may include one or more pairs of opposing force sensors 302a, 302b that detect and augment desired motions. For example, a first force sensor 302a may be positioned on the palmar surface of a finger and a second force sensor 302b may be positioned on a dorsal surface of the finger. Additionally or alternatively, a first force sensor may be positioned on a medial surface of the finger and a second force sensor may be positioned on a lateral surface of the finger. Force sensors 302a, 302b may be positioned on some or all fingers or portions of fingers in order to provide high fidelity sensing of desired movements.

Figure 3B:
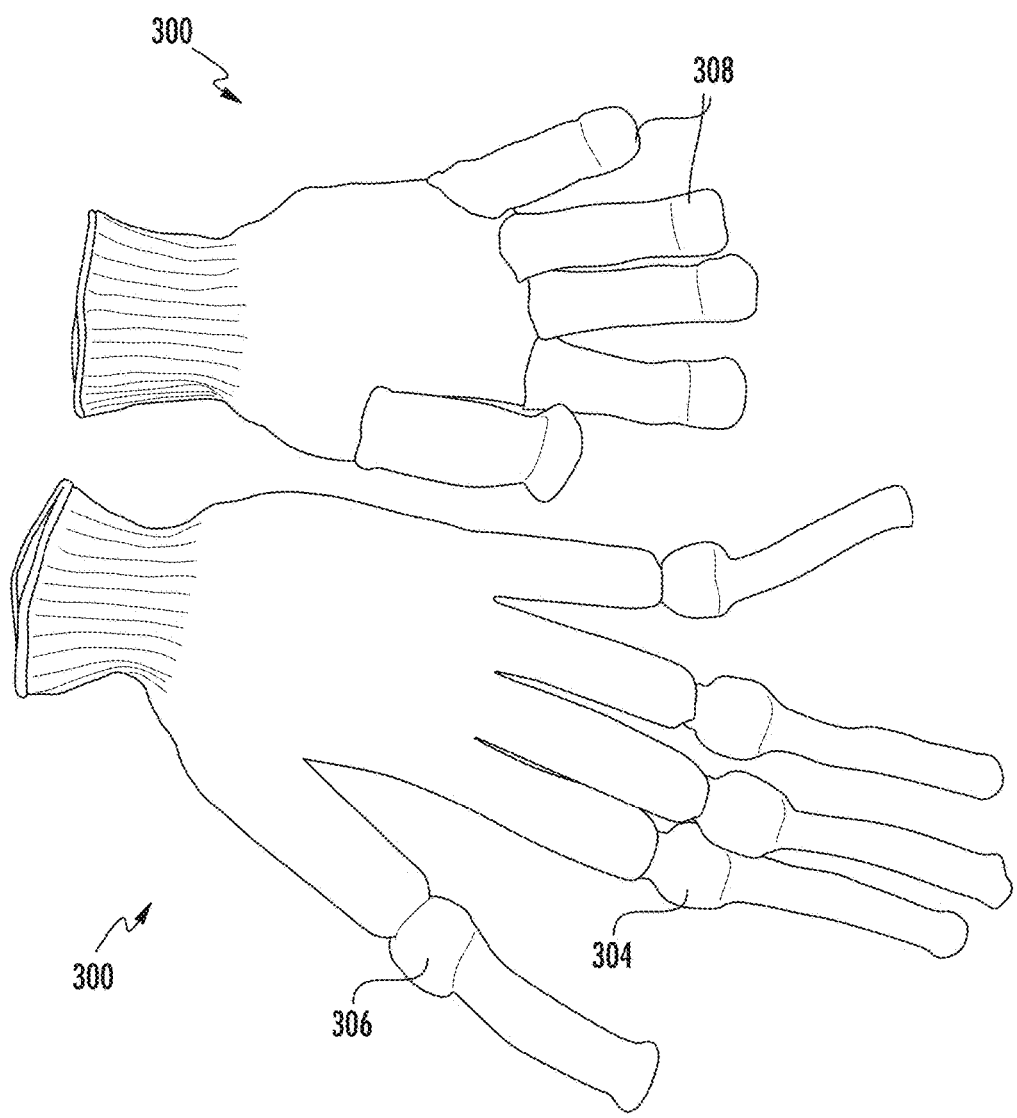
FIG. 3B depicts a pockets formed within gloves to receive force sensors.

Referring now to FIG. 3B, force sensors 302a, 302b may be positioned within pockets 304 formed by one or more protective layers of gloves (constructed from black yarn in FIG. 3B). The layers formed from black yarn may fold back over the fingers to protect and hide all electronic components.

Control Software and/or Hardware for Wearable Robotics

Another aspect of the invention provides control software and/or hardware for detecting forces applied to force sensors 302a, 302b determining desired characteristics of desired movement, and then controlling motors in order to move finger or other limb accordingly. For example, a controller may actuate motors for as long as a sufficient amount of force is applied to the relevant force sensor 302a, 302b.

Tactile Interactions with Computer-Generated Structures

Figure 4:
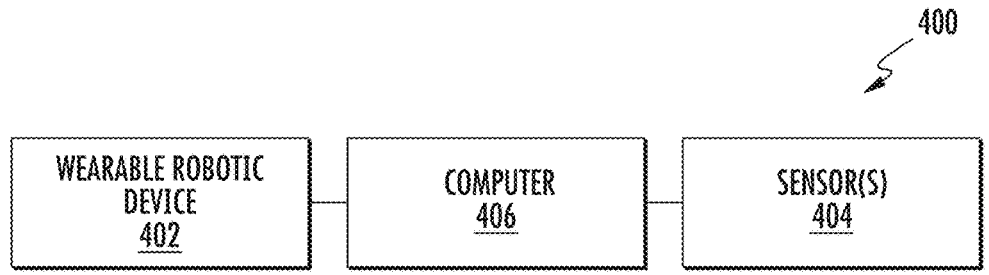
FIG. 4 depicts a system related to the glove described herein.

Referring now to FIG. 4, a system 400 for providing tactile interactions with computer-generated structures. System 400 includes wearable robotic device 402 such as the gloves described herein, one or more sensors 404, and a computer 406.

Sensor(s) 404 may be adapted and configured to detect a position of the glove 402 within a three-dimensional space. For example, sensor(s) 402 may detect and generate a three-dimensional point representing the location of each finger tip. Suitable sensors are available under the LEAP MOTION™ trademark from Leap Motion, Inc. of San Francisco, Calif. and described in U.S. Patent Application Publication Nos. 2013/182077, 2013/182079, 2013/182897, 2013/182902, and 2014/028861.

Figure 5:
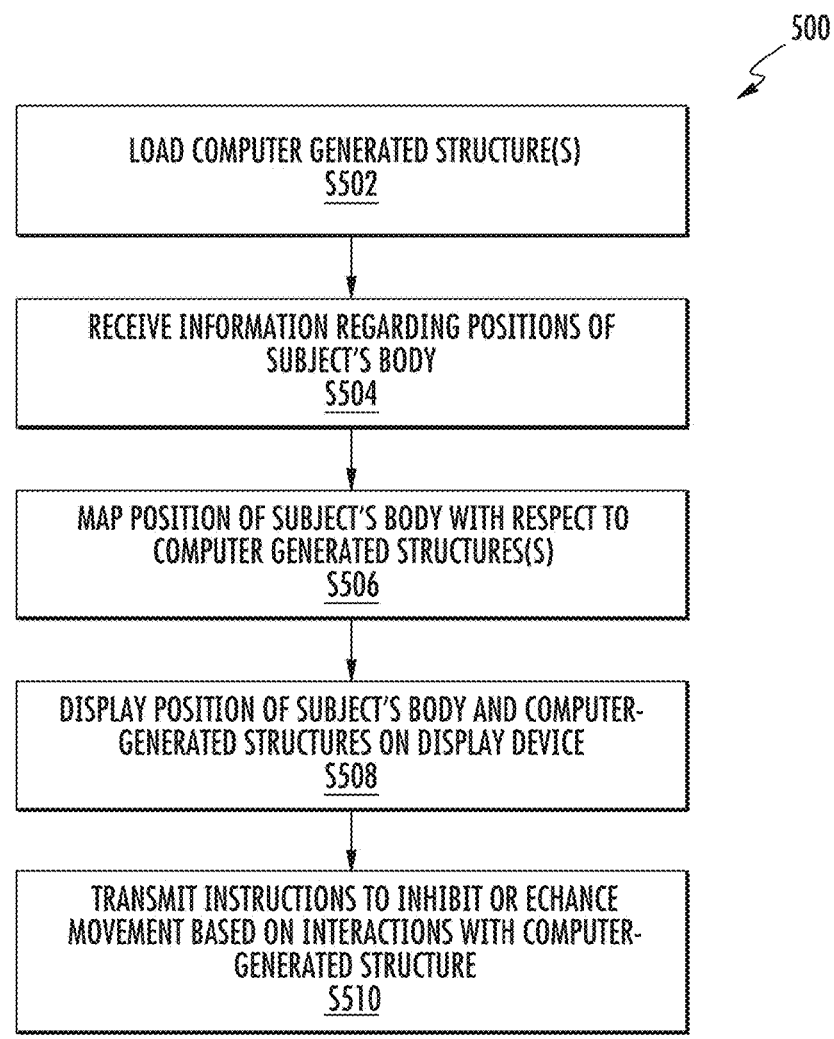
FIG. 5 depicts a method related to the glove described herein.

Computer 406 may be a general or special purpose computer containing instructions stored in hardware or software. An exemplary algorithm 500 is described below in the context of FIG. 5.

In step S502, the computer loads one or more computer-generated structures. The computer-generated structures may be 2-D or 3-D structures and may also include additional dimensionality that may be represented in display colors or through tactile feedback as will be discussed further herein. The computer-generated structures may be generated based on real-world data such as imaging or may be abstract elements created organically. For example, the computer-generated structures may be derived from medical or scientific imaging data produced using a technique such as magnetic resonance imaging (MRI), ultrasonography, positron emission topography (PET), computed tomography (CT), diffuse optical tomography, elastography, electrical impedance tomography, 3-D microscopy, 3-D confocal laser microscopy, and the like.

In step S504, the position of at least a portion of the subject's body is mapped with respect to one or more computer-generated structures. This information may be determined using sensor(s) 404 as discussed above.

In step S506, the position at least a portion of the subject's body is mapped relative to the one or more computer-generated structure. For example, computer 406 may determine whether a point associated with any of the subject's fingers lies outside, within, or adjacent to a computer-generated structure.

In step S508, the computer 406 displays the position of at least a portion of the subject's body and the computer-generated structures on a display device. The position of the subject's body may be depicted as one or more points or may include an image of the relevant body parts (e.g., fingers or hands).

In step S510, the computer 406 controls the one or more actuators in the glove 402 to inhibit, enhance, augment, and/or induce movement based on interactions with the computer-generated structures and/or other subjects using system 400.

For example, computer 406 may control actuators to inhibit movement of the subject's fingers if the subject contacts a computer-generated object in a similar manner to a desk applying upward force to one's fingers if the fingers contact a fixed object while a hand is moving downward. This feature may advantageously enhance the subject's interactions with the computer-generated structures. Additionally, this aspect of the invention allows the subject to interact with structures that are outside of the subject's field of view. For example, a subject could move his virtual hand behind a computer-generated structure (e.g., a structure representing a human stem cell) to feel the surface geometry of the rear of the structure and/or where and how the structure interfaces with other structures (e.g., blood vessels). Additionally, this enables a subject to virtually interact with the physical properties of a structure such as the structure's rigidity. For example, certain structures may have a spongy surface that is represented to the subject by providing less resistance to movement of the subject's fingers. Other structures may have more rigid surfaces that produce a more pronounced resistance to movement of the subject's fingers.

In another example, movement may be enhanced. For example, a subject's fingers may be moved to physically represent fluid or ion flows or to draw the subject's fingers in the direction of various gradients. In another example, the subject's fingers may be drawn towards interesting image regions and/or regions of an image that the subject has not yet examined in detail. In still another example, vibrotactile sensor may provide vibrations of varying patterns and/or intensity to represent additional dimensions of data such as temperature, biological activity (e.g., as detected through fluorescent imaging), electrical potential, radioactivity, and the like. In yet another embodiment, a subject's fingers may be manipulated by another user (e.g., for teaching or demonstration purposes). Additionally or alternatively, feedback provided to one subject may be provided to other subjects.

The feedback provided to the subject may be user-definable. For example, if a complex image was produced using a plurality of fluorescent probes (each representing different biological activities), the subject may select one or more fluorescent signals for representation through tactile feedback. Likewise, the overall intensity of feedback and/or the mapping of amplitudes of signals in the image data to tactile feedback may be adjusted by the subject.

Figure 6:
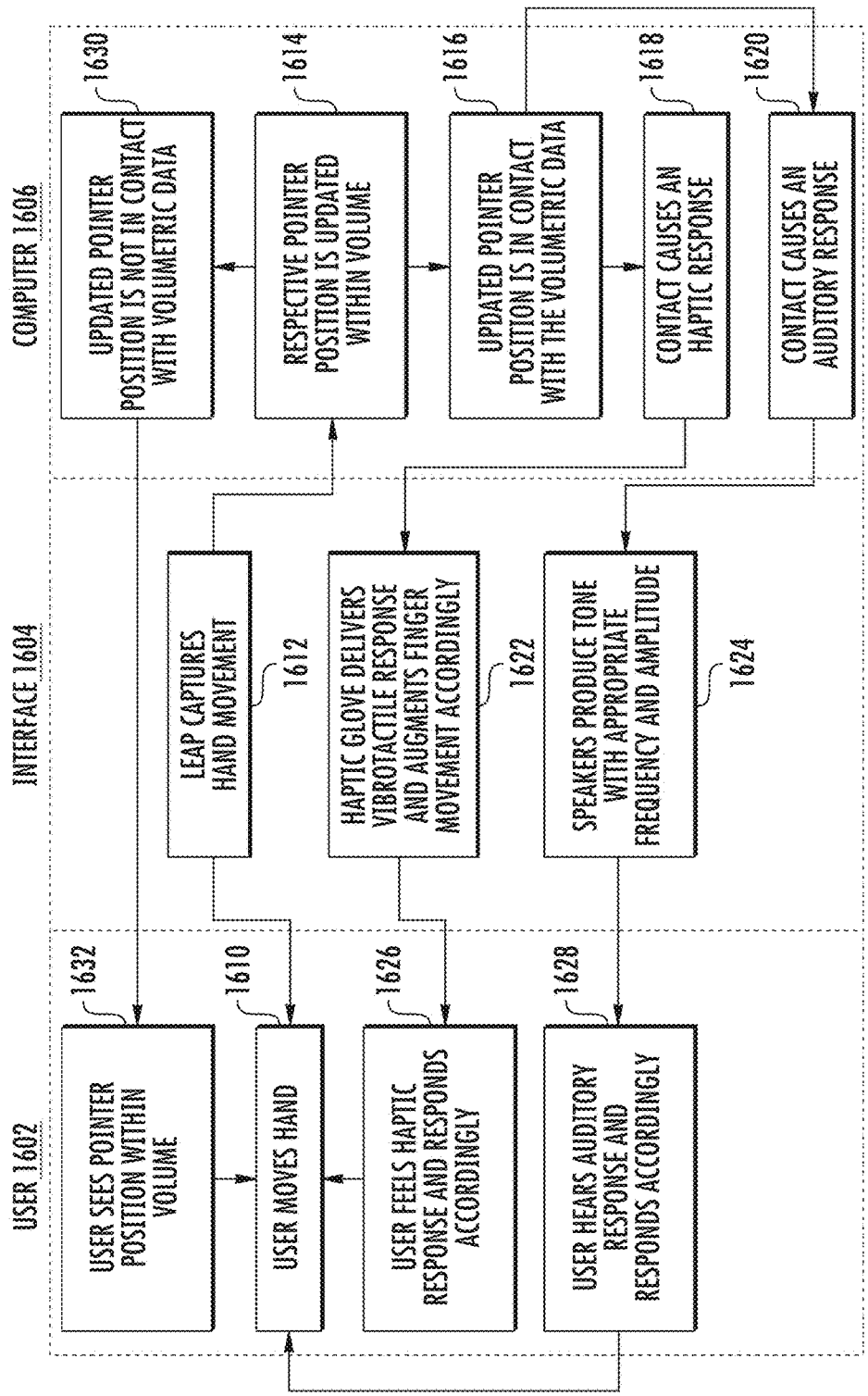
FIG. 6 depicts interactions between a user, an interface and a computer.

FIG. 6 depicts interactions between a user, an interface and a computer. When a user moves their hand 1610, the Leap interface 1604 captures the hand movement 1612 and the computer 1606 updates a pointer within a defined volume 1614. If the updated pointer position is in contact with the defined volumetric data 1616, the contact causes both a haptic response 1618 and auditory response 1620, which result in the interface 1604 delivering haptic feedback 1622 or audible feedback 1624 accordingly. The user feels 1626 or hears 1628 each of these and may respond accordingly. If the updated pointer position is not in contact with the volumetric data 1630, the user sees the pointer position and 1632 and moves their hand accordingly.

Figure 7:
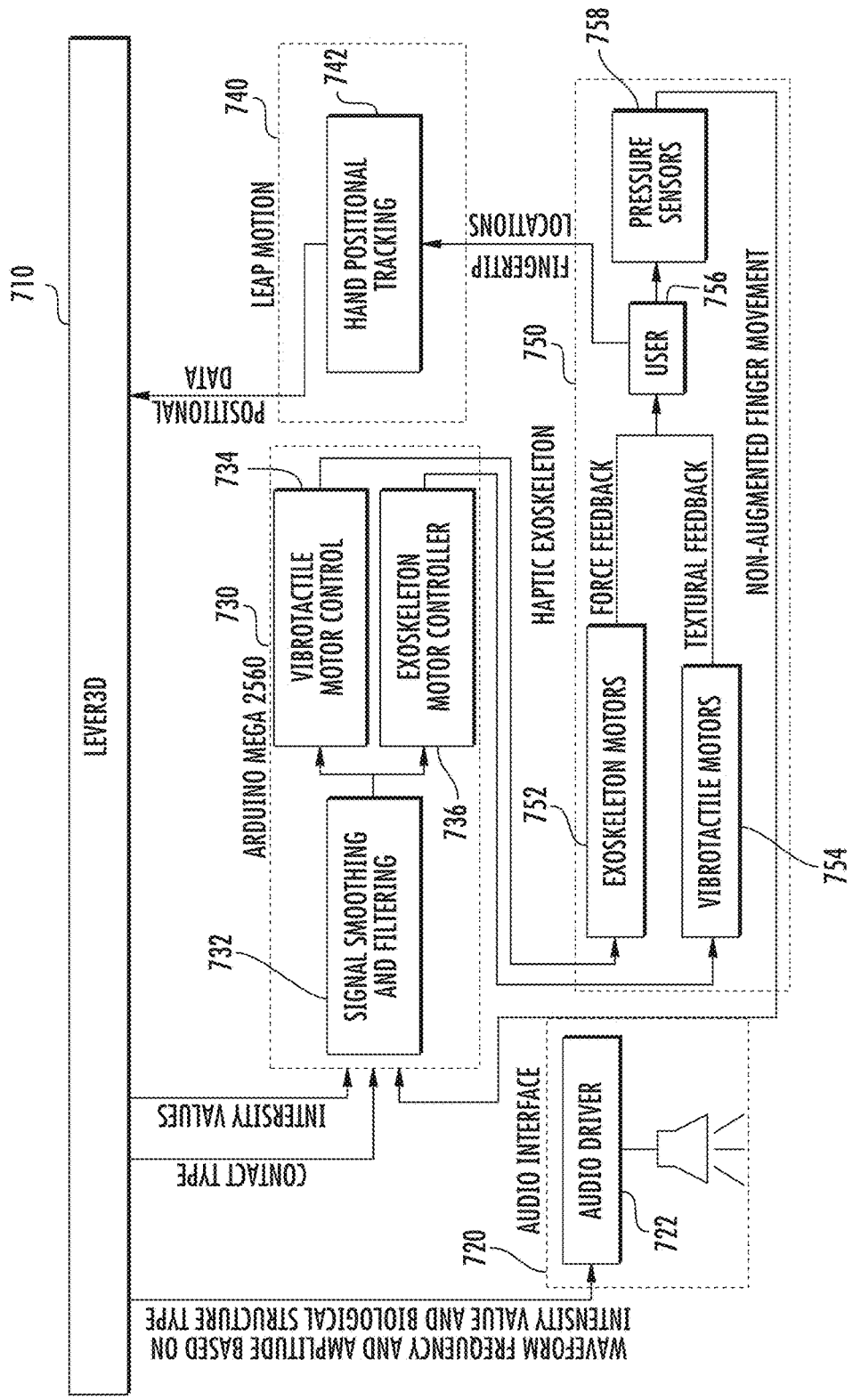
FIGS. 7 and 8 depict data flows within and between components.
Figure 8:
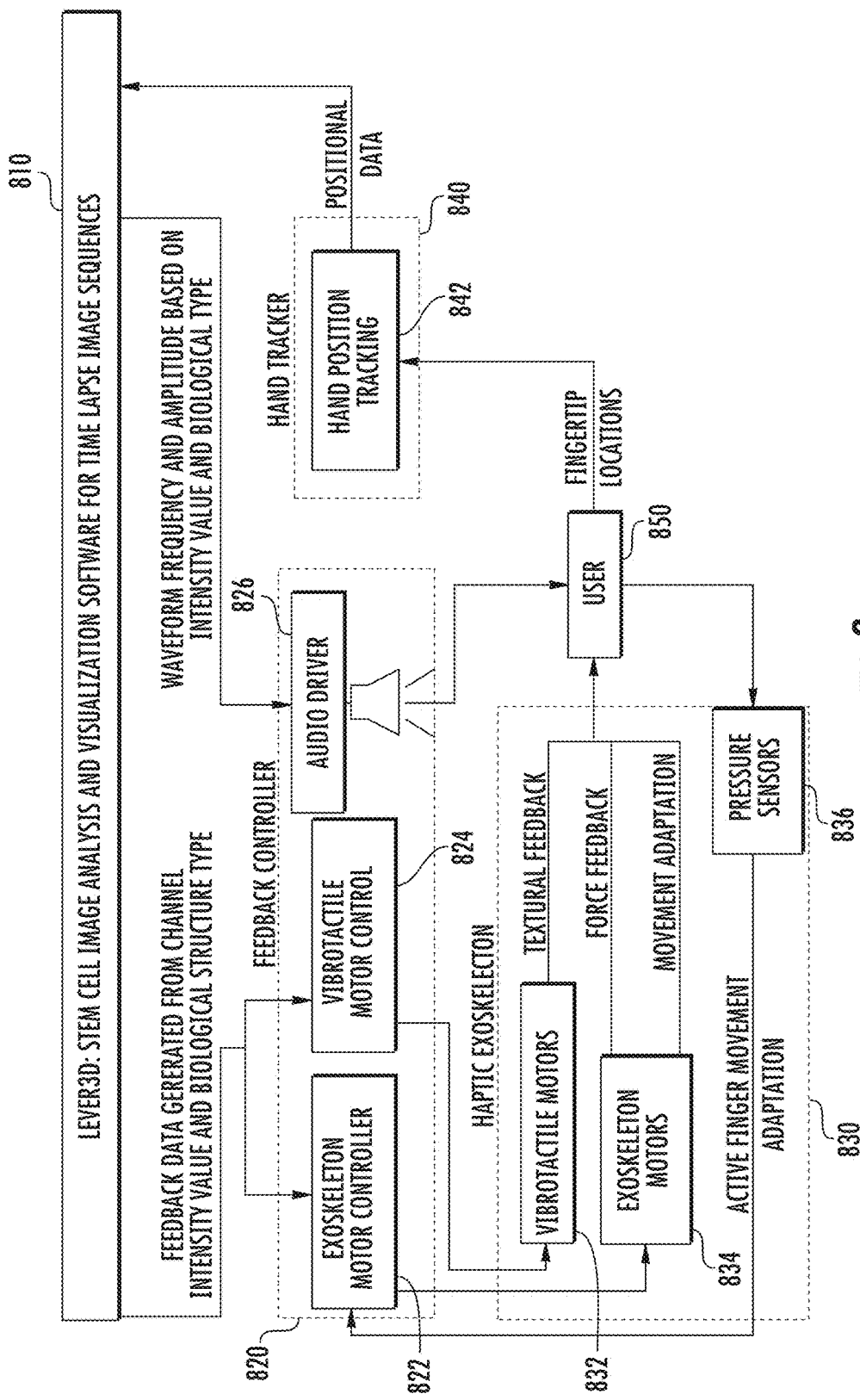

FIGS. 7 and 8 depict data flows within and between components. FIG. 7 shows the Lever3D in communication with the audio interface 720, Arduino Mega 2560 730, Leap Motion 740, and Haptic Exoskeleton 750. The Lever3D 710 provides waveform frequency and amplitude based on intensity value and biological structure type to an audio driver 722 in the audio interface 720. The Lever3D also provides contact type and intensity values to the signal smoothing and filtering device 732, which is further in communication with the vibrotactile motor control 734 and exoskeleton motor control 736.

The motor controls 734, 736 communicate with the Haptic exoskeleton 750 exoskeleton motor 752 and vibrotactile motors 754 respectively. These motors 752, 754 provide force and textural feedback to a user 756, whose fingertip locations communicate with the leap motion 740 hand position tracking 742.

The user 756 communicates with pressure sensors 758, which in turn communicate with the Mega 2560 730.

FIG. 8 shows the Lever3D stem cell image analysis and visualization software for time lapse sequences 810 in communication with various devices including a feedback controller 820 a haptic exoskeleton 830, and hand tracker 840. The Lever3D software 810 provides feedback data generated from channel intensity value and biological structure type to the exoskeleton feedback controller 822 and vibrotactile controller 824. The controllers 822, 824 communicate with the motors 832, 834 that communicate textural feedback, force feedback, and movement adaptation to the user 850. The user 850 communicates with the pressure sensors 836 that communicate active finger movement adaptation to the exoskeleton motor controller 822.

The user's fingertip locations are communicated to the hand tracker 840 hand position tracking 842 that communicates position data to the Lever 3D software 810. The Lever3D software may also communicate waveform frequency and amplitude based on intensity value and biological type to the audio driver 826, which in turn communicates with the user 850.

Figure 9:
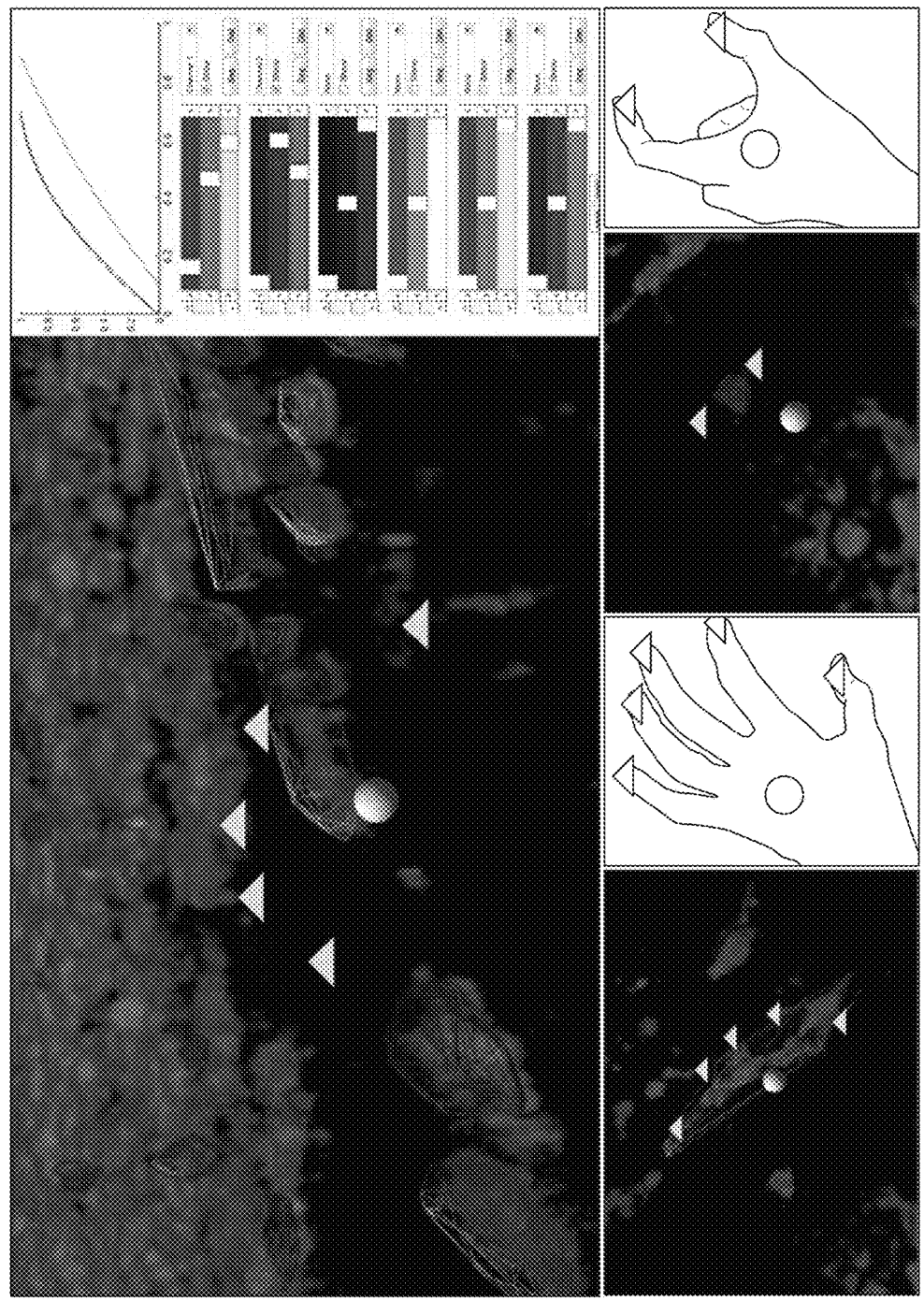
FIGS. 9 and 10 provide screenshots of a user-interface.
Figure 10:
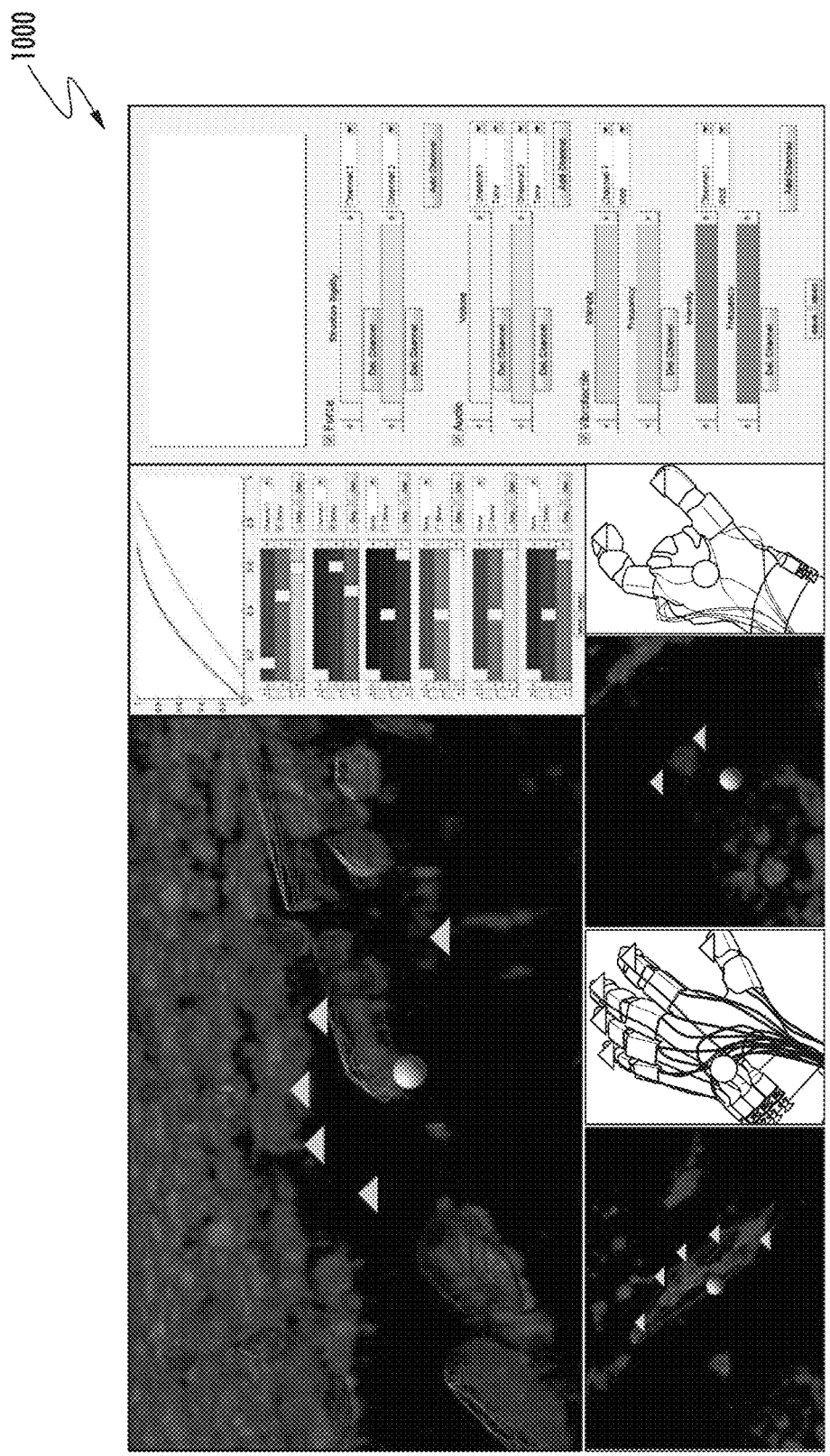

FIGS. 9 and 10 provide screenshots of a user-interface 900, 1000.

Additional Glove Embodiments

Figure 13A:
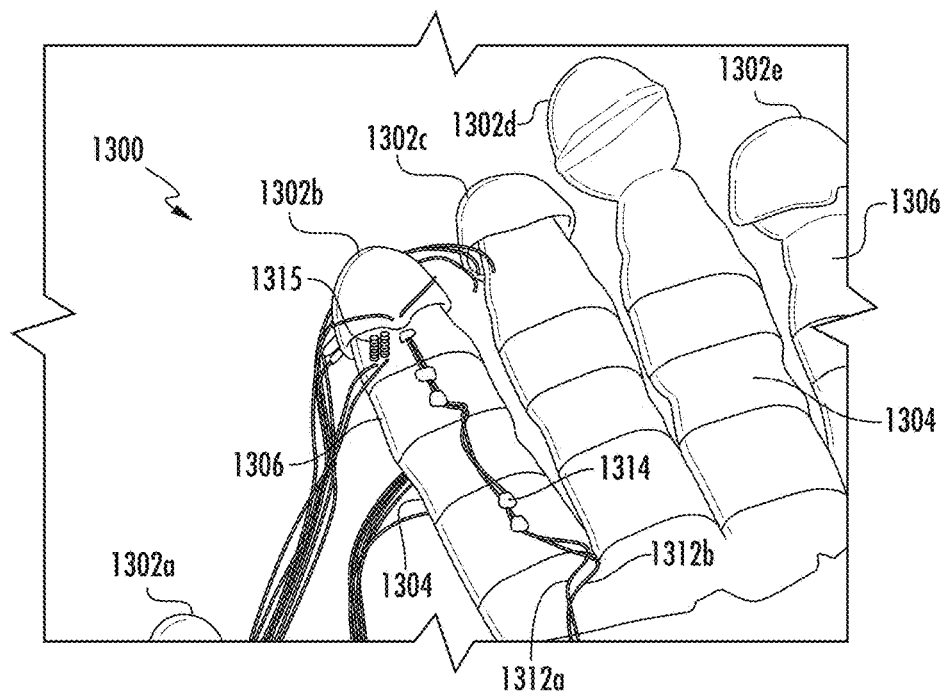
FIGS. 13A and 13B depict a different glove.

Referring now to FIG. 13A, another glove 1300 is provided including a plurality of fingers 1302. As in the glove depicted and described in the context of FIGS. 1A and 1B, each of the fingers 1302a-e may include one or more compliant regions 1304 and flexible, but less compliant regions 1306 (fabricated from white yarn in FIG. 13A).

The fingers 1302 may have a single-fabric-layer construction. In some embodiments, the finger tips may include additional fabric layers shown in the unfolded shape on finger 1302d and in the folded arrangement on fingers 1302b, 1302c, and 1302e.

Figure 11A:
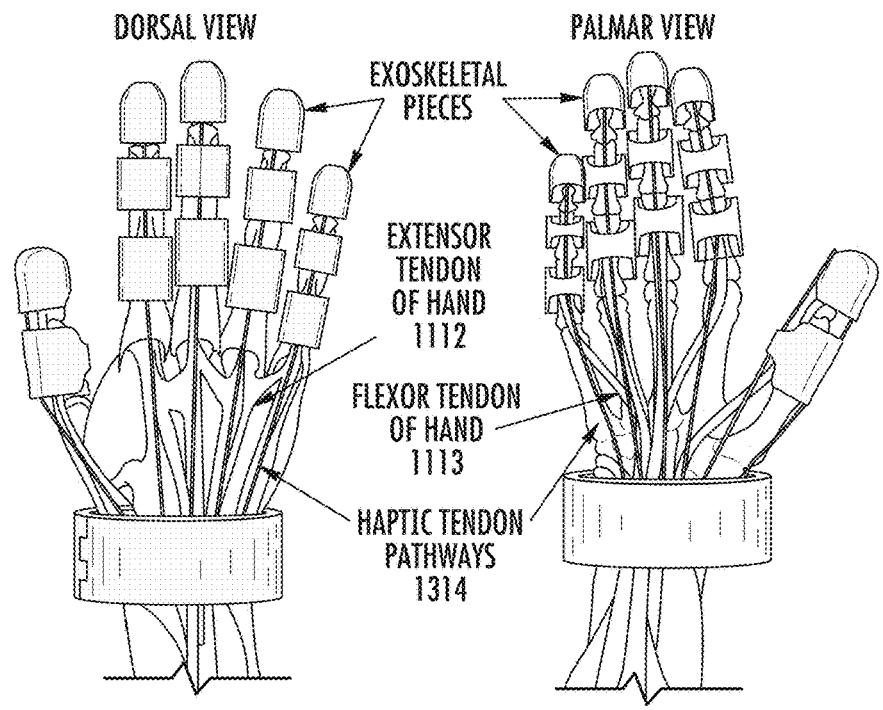
FIGS. 11A and 11B depict the parallel structures between haptic tendons and anatomical tendons.
Figure 11B:
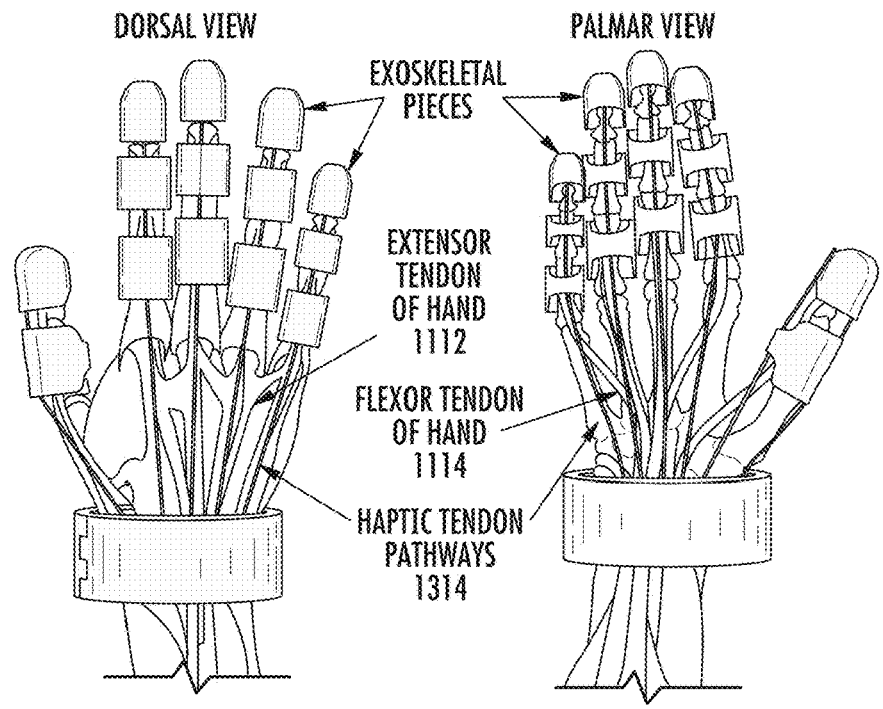

Still referring to FIG. 13A, tendons 1312a, 1312b may loop around the each finger tip connected to the glove 1300 via pathways 1314 before connecting to an actuator. The tendons 1312a, 1312b shown in the dorsal side of fingers 1302a-1302e (and actuated to extend the fingers) may travel to the ventral side of the finger tip before returning to the ventral side and traveling along the same channels to the actuator so that two tendon strands 1312a, 1312b run in parallel along channels within the glove 1300 to an actuator. In a similar manner, ventral tendons actuatable to flex the fingers may loop around the dorsal side of the fingertip. (FIGS. 11A and 11B depict the parallel structures between haptic tendons 1314 and anatomical tendons like the extensor tendon 1112 and flexor tendon 1114.) In another embodiment, the tendons 1312a, 1312b may terminate on the sides of the fingertips or in any other location on the fingertips of the glove 1300.

Force sensors 1315 as depicted in and described in the context of FIG. 3A may be incorporated within the fabric (e.g., between folded layers). For example, force sensor 1315 may be coupled to the fabric using an adhesive such as silicon epoxies.

Figure 13B:
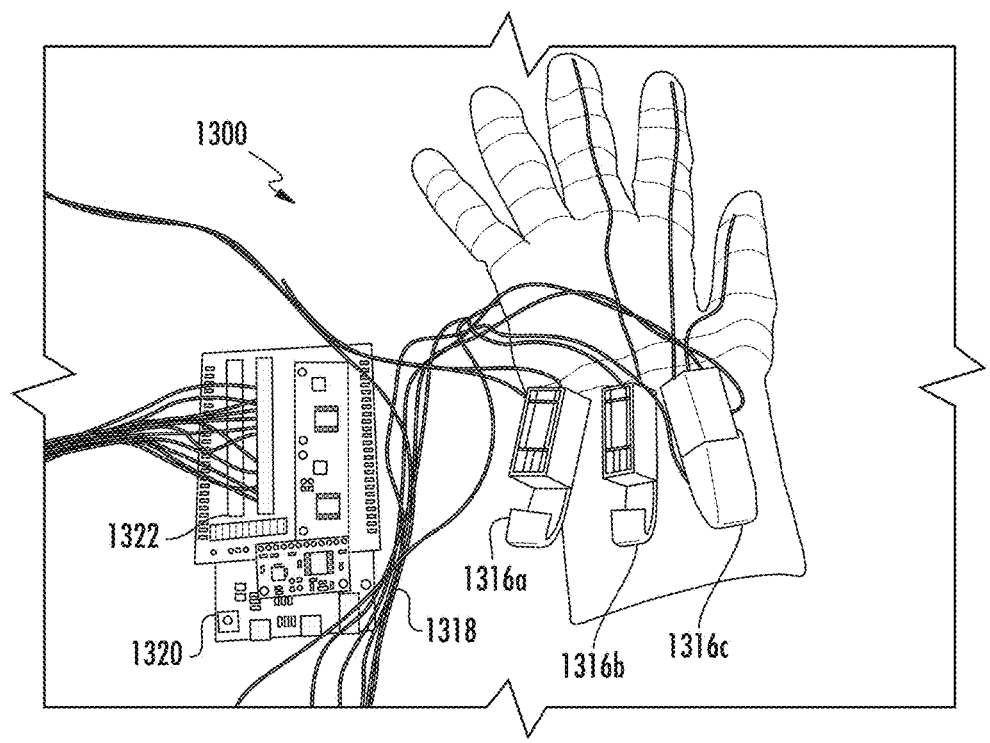

Referring now to FIG. 13B, tendons 1312 may be coupled to actuators 1316a, 1316b, 1316c. Actuators 1316a-c may be removably mounted on the wrist or the back of the hand, e.g., using hook-and-loop fastening systems such as those available under the VELCRO® and VELSTRETCH® trademarks from Velcro Industries B.V. of the Netherlands Antilles. This modular system allows for actuators to be added or removed from a glove to reflect situational needs.

Leads 1318 from each actuator 1316a-c may be gathered in a bundle interface with a control device 1320 (e.g., an ARDUINO® microcontroller or other printed circuit board) via an interface 1322 (e.g., a wired interface such as a 36 pin-out female header, a USB interface, and the like or a wireless interface). Control device may include or more (e.g., 5, 10, and the like) serial controls each adapted and configured to control operation of one or more actuators. Control device 1320 may further interface with a computer through an additional interface such a serial port or a USB port. The computer may further control operation of the control device 1320 and glove 1300 through software and/or hardware. For example, code for serial communications with the control device 1320 and storage of data in a dynamic struct may written in the C++ programming language. Exact tendon lengths and fingertip interactions may be continuously updated and made available for further processing in programs such as MATLAB® software available from The MathWorks, Inc. of Natick, Mass. The C++-based software may interface with the MATLAB® software via one or more MEX interfaces defined by the MATLAB® software. The MATLAB® software may process and display the data in real time to provide information such as joint range of motion and capable pressure.

Figure 12:
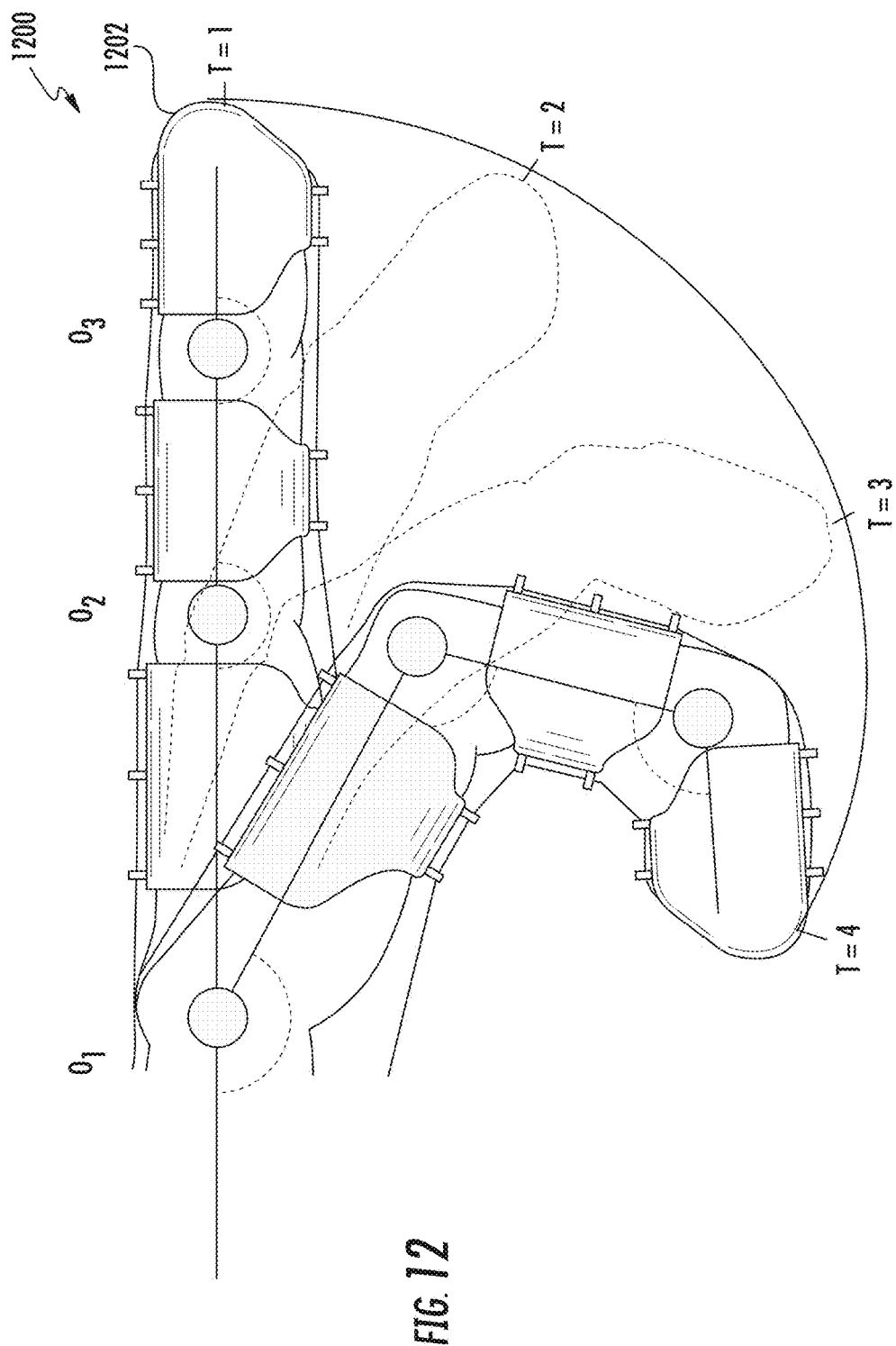
FIG. 12 depicts flexion of a wearable robotic device.

FIG. 12 depicts flexion of a wearable robotic device 1200 moving a finger 1202 between positions T=1, T=2. T=3, and T=4.

Figure 14A:
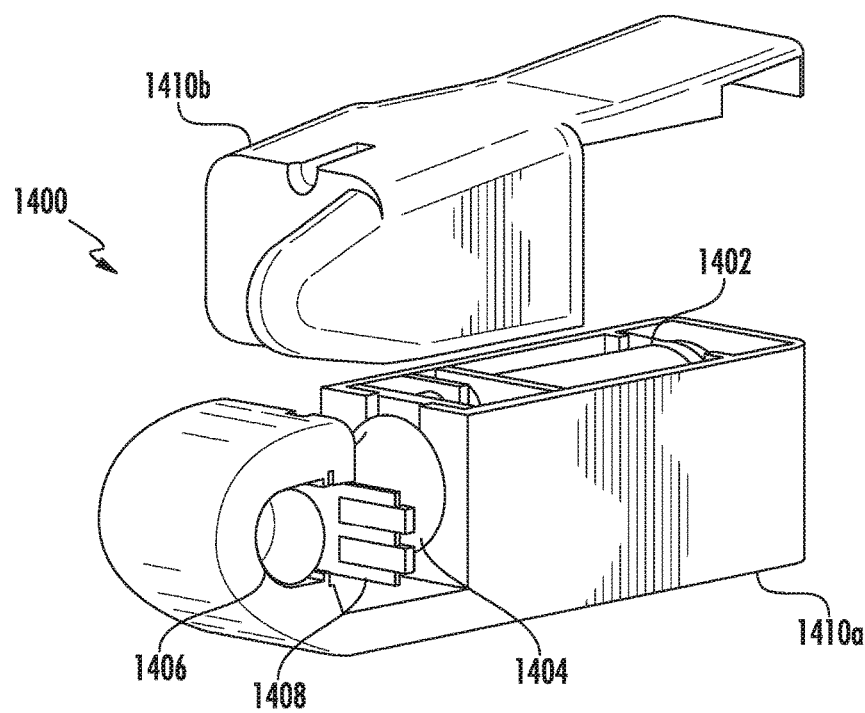
FIGS. 14A and 14B depict an actuator.
Figure 14B:
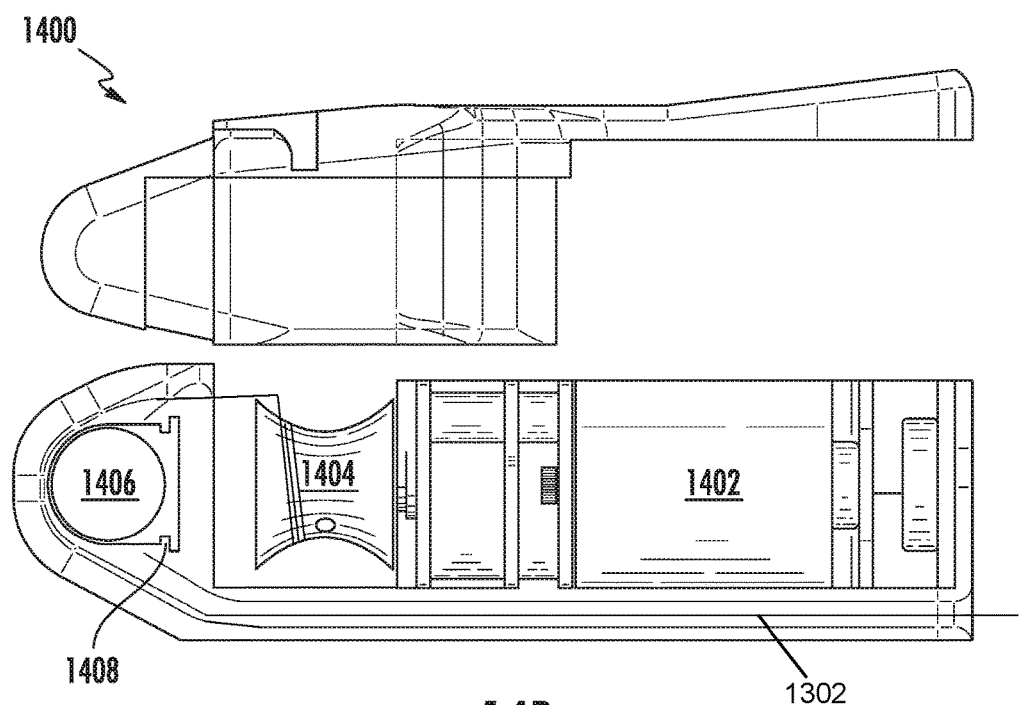

Referring to FIGS. 14A and 14B, actuators 1400 may include a motor 1402 and a winch 1404 as depicted in and described in the context of FIG. 2. Actuator 1400 may further include a free-floating tensioning drum 1406 over which the tendon 1312 passes. Tensioning drum 1406 may sit adjacent to a force sensor 1408 such as a strain gauge or a piezoresistive force sensor adapted and configured to measure the amount of force applied by the tendon 1312 to the tensioning drum 1406. Such measurements may be utilized both as feedback to control operation of the motor 1402 and to sense movement by the user, which will manifest itself as increased force measurements in some actuators 1400 when tendons are extended and decreased force measurements on actuators 1400 coupled to opposing tendons 1312. Motor 1402 may include an encoder (e.g., a magnetic encoder) that converts the angular position of the motor into electrical signals. In one embodiment, the encoder has 600-count (or 0.6°) resolution. In one embodiment, the motor 1402 is a servomotor. Covers 1410a, 1410b allow the tendon(s) 1312 to enter the actuator, while protecting internal components 1402, 1404, 1406, 1408.

Figure 15:
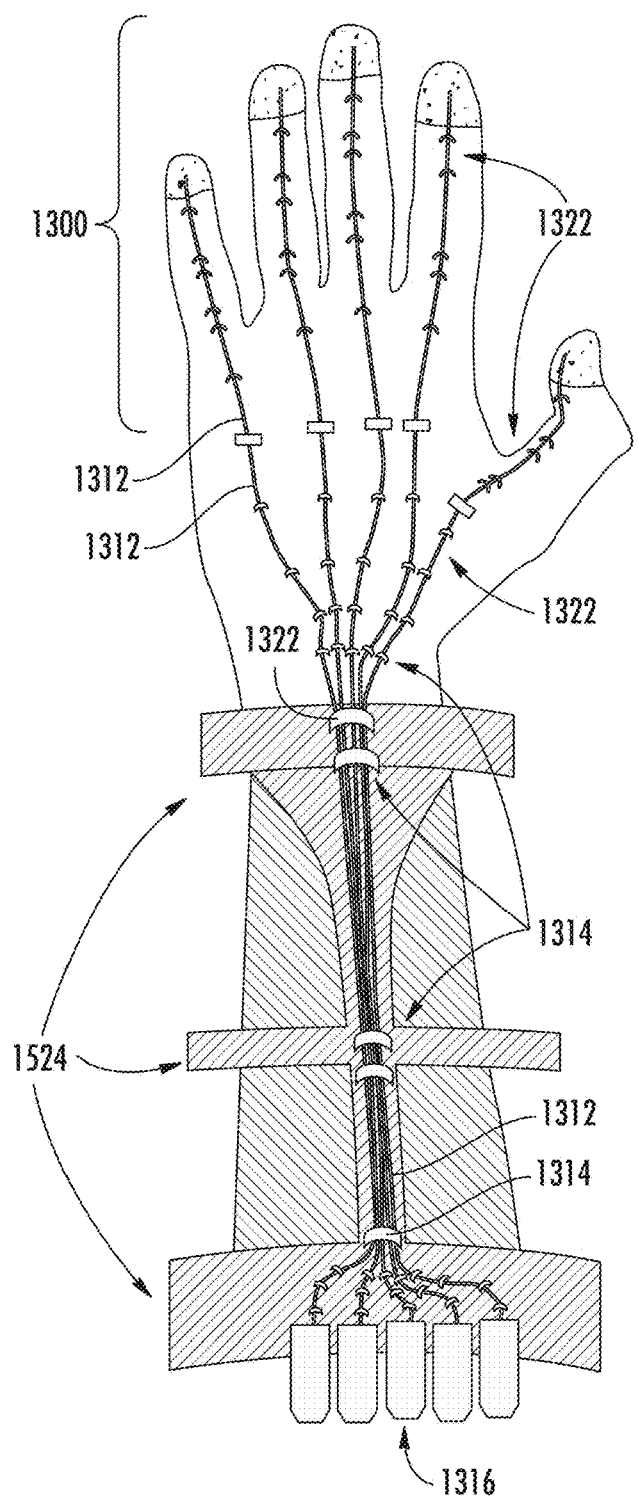
FIG. 15 depicts a system in which actuators are mounted remotely from a glove.
Figure 16A:
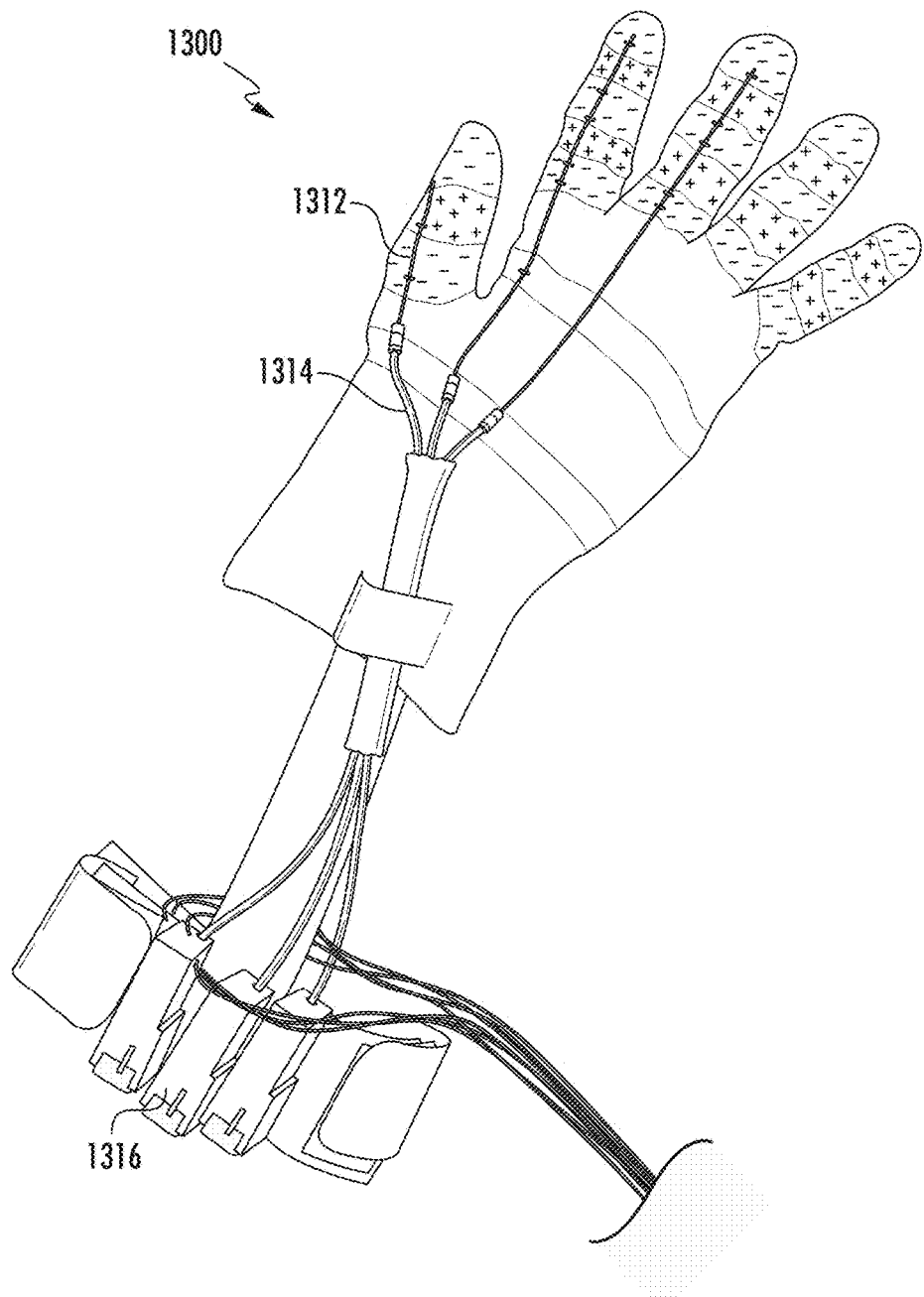
FIGS. 16A-16C are photographs of a system in which actuators are mounted remotely from a glove.
Figure 16B:
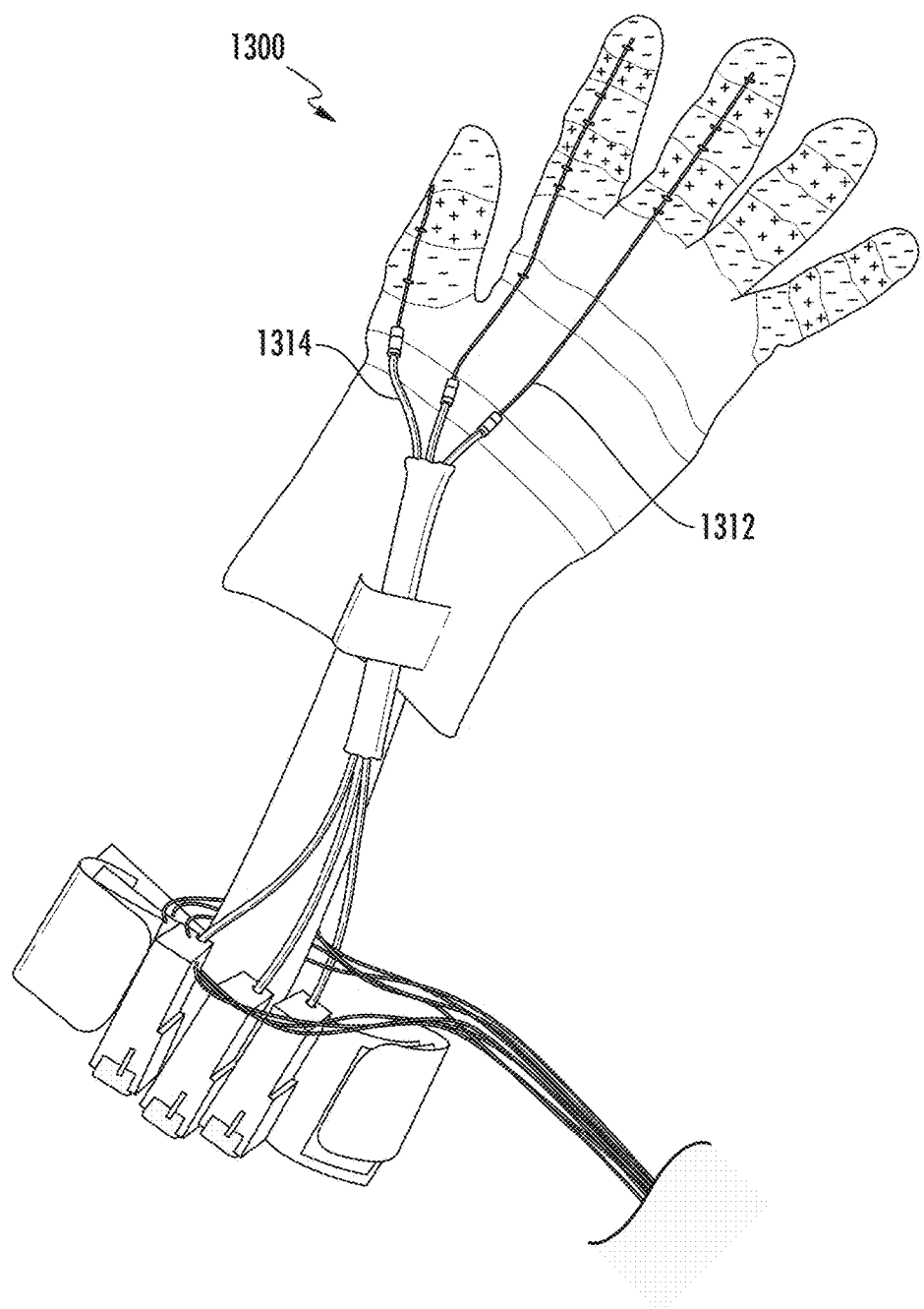
Figure 16C:
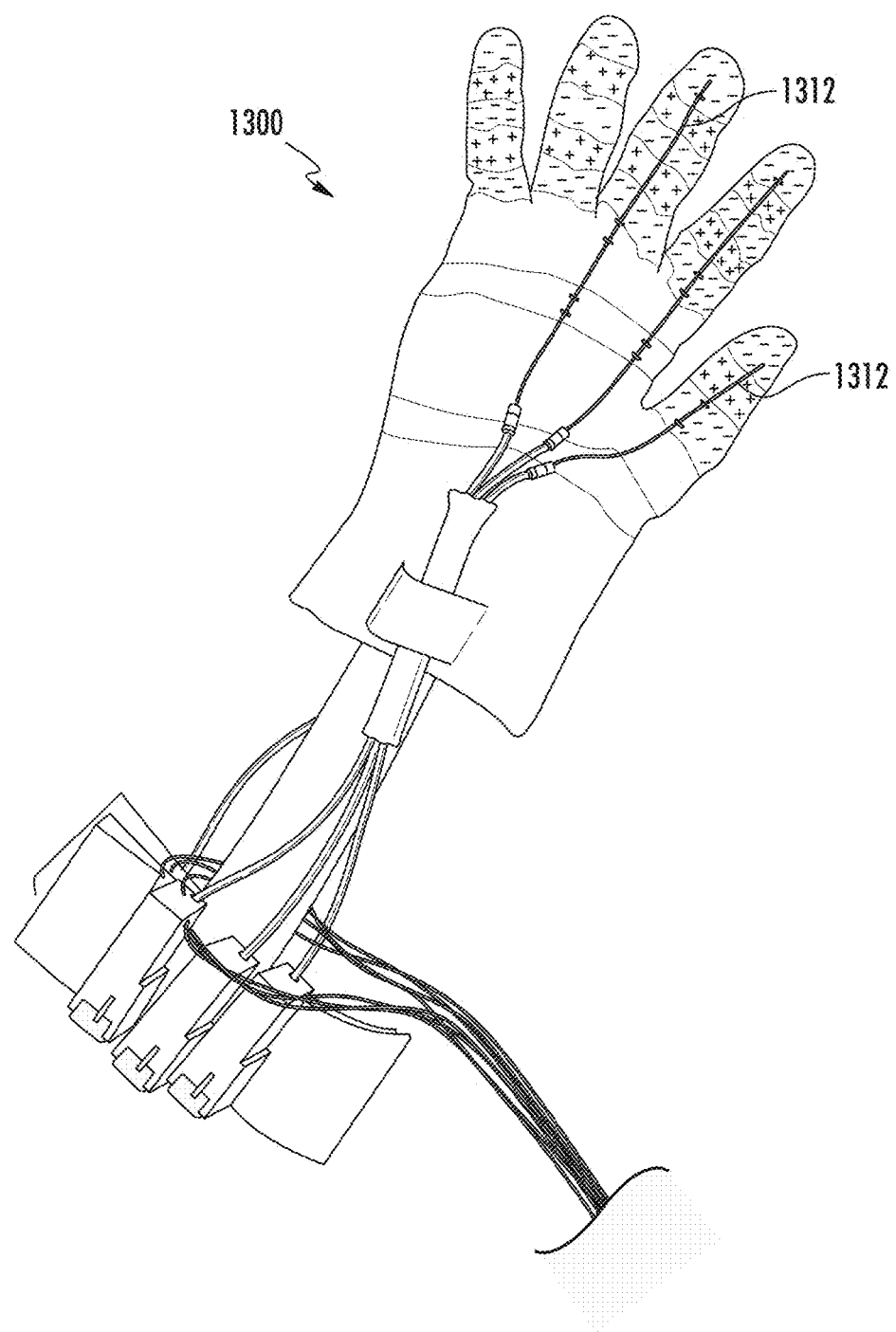

Actuators 1316, 1400 may be positioned at various locations, both on the glove/garment or off. FIG. 15 depicts one such embodiment in which the actuators 1316 are positioned on the forearm near the user's elbow. The tendons 1312 may extend along the forearm to the fingers through sheaths 1522. Sheaths 1522 may be designed for low friction and/or fabricated from low friction materials such as polytetrafluoroethylene (PTFE) and may be fabricated using techniques such as extrusion, weaving, and the like.

This will free the wrist and allow greater room for placement of additional actuators 1316. The additional actuators 1316 will facilitate more intricate exercises and allow for more diverse functionality. For example, four tendons 1312 running to the tip of each finger may facilitate and track every aspect of fingertip motion in 3D space. Alternately, three tendons 1312 running to each finger may exert assistive torque on the MCP vs. PIP/DIP joints independently. Sheaths 1524 (and tendons 1312 received therein) may run directly from the actuator housing via knit structures 1314 in a biomimetic implementation. The tendons 1312 may slide without perceptible friction through routing tubes 1322 (similar to a sheathed bicycle brake cable) and emerge at the base of the finger where they may exert force along the rest of the tendon pathway. Sheaths 1322 may be supported along the forearm using one or more bands 1524, which may be releasably attached to the arm using a releasable closure such as hook-and-loop fastening systems such as those available under the VELCRO® and VELSTRETCH® trademarks from Velcro Industries B.V. of the Netherlands Antilles. In one embodiment, the actuators may be placed in a back pack, lumbar pack, or other wearable pouch.

Scalability of Gloves and Garments

The gloves 100, 1300 and other garments described herein may be produced in a knit in a single size and then stretched to desired size using a complementary mold before treating flexible, but less compliant regions 106, 1306.

Applications of the Invention

The wearable robotic device may be used in rehabilitation of a subject by assisting the subject's attempts to move their fingers and thereby maintaining muscle tone without the need for a physical therapist's direct manipulation of the subject's body. For example, the resistance applied by motors may be controlled to apply varying resistance to movement of a limb. Additionally or alternatively, the forces applied to the motors may be measured to assess a subject's strength. Measurements from the glove may be recorded, transferred, and/or stored (e.g., in an electronic medical record) and may be used to track a subject's progress towards goals in a training and/or rehabilitation program. Additionally, measurements may be aggregated, for example, from several clients on a server, to produce baseline, model, or reference data for particular demographics (e.g., women between 70 and 75 years of age). Movements in response to particular exercise regimens may be recorded and analyzed for strength, proper form, speed, and the like. Although hand exercises may benefit the general public, rock climbers, gymnasts, weight lifters, and musicians (e.g., pianists, percussionists, string players, woodwind players, and brass players) may particularly benefit from such exercises. Additionally, the principles described herein may be incorporated into gloves used for golfing and/or baseball to measure whether the flexion of the subject's fingers is appropriate and/or to apply force to show the user the appropriate grip. Moreover, the principles herein may be utilized in other garments and/or soft robotics to measure positioning, force, movement, and/or form and provide biofeedback and/or training to a user.

The gloves and devices described herein may be used in space suits worn by astronauts and configured to provide a desired amount of resistance to movements of the astronaut while in orbit in order prevent or reduce the occurrence of muscle atrophy and/or spaceflight osteopenia due to weightlessness. The glove may also be used as a haptic device to control robotics (e.g., during space walks).

The gloves and devices described herein may be used in flight suits worn by pilots (e.g., fighter pilots) to provide additional strength when facing high G-forces during maneuvers.

The glove may be used as an industrial tool for factory line workers. The system may provide grip assistance when additional strength is needed and/or monitor the actions of the worker's hand (e.g., to to prevent injury due to repetitive harmful movements that may be captured with the glove).

The glove may be the used by persons with complete loss of hand functionality to control a compromised hand, thereby giving the user the ability to use it again.

The glove and control device are part of a distributed system in which a local client (e.g., written in JAVASCRIPT®, JAVA®, C++, MATLAB®, and the like) controls the user's interactions with the glove to exert and/or measure force and or location of the glove during a session. A medical professional (e.g., a therapist) may optionally monitor the user's performance synchronously or asynchronously. The medical professional may consult with models of strength and range of motion appropriate for the patient and/or may define one or more goals for the user. The user may further use the client, a portal, or a smartphone, tablet, or computer application to view their history, monitor their progress toward goals, interact with a medical professional, and the like. All information about the user's performance, the medical professionals treatment parameters, and the like may be stored in and communicated via a server. This server may facilitate integration with an electronic medical record system.

The wearable robotic device may be used in various industrial, law enforcement, and military applications to enhance the subject's physical abilities.

Additionally, the tactile feedback aspects of the invention may be used to facilitate control of a robotic device. For example, the subject may be a surgeon controlling the operation of robotic surgery system, a mechanic controlling a robotic device to repair a difficult-to-reach component, a bomb technician diffusing an explosive device (e.g., using a robotic device such as those available from iRobot Corporation of Bedford, Mass.), and the like.

Moreover, the glove may be used in simulation, training, or video gaming applications. For example, the subject may utilize a glove as described herein to interact with a virtual environment, e.g., by grasping and twisting a door knob, handling a weapon, holding a baseball, and the like.

The functions of several elements may, in alternative embodiments, be carried out by fewer elements, or a single element. Similarly, in some embodiments, any functional element may perform fewer, or different, operations than those described with respect to the illustrated embodiment. Also, functional elements (e.g., modules, computers, and the like) shown as distinct for purposes of illustration may be incorporated within other functional elements, separated in different hardware, or distributed in a particular implementation.

While certain embodiments according to the invention have been described, the invention is not limited to just the described embodiments. Various changes and/or modifications may be made to any of the described embodiments without departing from the spirit or scope of the invention. Also, various combinations of elements, steps, features, and/or aspects of the described embodiments are possible and contemplated even if such combinations are not expressly identified herein.

The entire contents of all patents, published patent applications, and other references cited herein are hereby expressly incorporated herein in their entireties by reference.

The invention claimed is:

1. A wearable device comprising:
    at least one compliant textile region adapted and configured to be placed over a joint of a subject; and
    at least two flexible but less compliant textile regions coupled to opposite ends of the compliant region located on either side of the joint and encircling the joint;
    wherein the at least two flexible but less compliant textile regions are steam hardened.

2. The wearable device of claim 1, wherein the at least one compliant textile region comprises a textile including one or more fibers selected from the group consisting of: natural fibers, cotton, wool, silk, hemp, flax, animal hair, jute, modal, cellulose, bamboo, piña, ramie, nettles, milkweed, seaweed, metals, manufactured fibers, azlon, acetate, triacetate, viscose, lyocell, glass, graphite carbon, carbon fiber, carbon nanotube, liquid crystal, ceramics, polyesters, aramids, para-aramids, meta-aramids, aromatic polyesters, rayon, acrylics, modacrylics, polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nytril, elastoester, nylon, spandex/elastane, olefins, biosynthetic polymers, and blends of the same.

3. The wearable device of claim 1, wherein the at least one compliant textile region comprises an elastomer.

4. The wearable device of claim 1, wherein the at least one compliant textile region is capable of elongation between 160% and about 180%.

5. The wearable device of claim 1, wherein the at least two flexible but less compliant textile regions-include one or more fibers selected from the group consisting of: natural fibers, cotton, wool, silk, hemp, flax, animal hair, jute, modal, cellulose, bamboo, piña, ramie, nettles, milkweed, seaweed, metals, manufactured fibers, azlon, acetate, triacetate, viscose, lyocell, glass, graphite carbon, carbon fiber, carbon nanotube, liquid crystal, ceramics, polyesters, aramids, para-aramids, meta-aramids, aromatic polyesters, rayon, acrylics, modacrylics, polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nytril, elastoester, nylon, spandex/elastane, olefins, biosynthetic polymers, and blends of the same.

6. The wearable device of claim 1, wherein the at least two flexible but less compliant textile regions are capable of elongation between 91% and 111%.

7. The wearable device of claim 1, wherein the at least one compliant textile region and at least two flexible but less compliant textile regions are made from the same textile material.

8. A wearable robotic device comprising:
at least one compliant textile region adapted and configured to be placed over a joint of a subject; and
at least two flexible but less compliant textile regions coupled to opposite ends of each compliant textile region and encircling the joint; and
at least one actuator adapted and configured to move the flexible but less compliant textile regions relative to each other.

9. The wearable robotic device of claim 8, wherein the at least one actuator facilitates a movement of the joint selected from the group consisting of: flexion, extension, abduction, and adduction.

10. The wearable robotic device of claim 8, wherein the actuator includes an artificial tendon.

11. The wearable robotic device of claim 8, wherein the actuator includes elements selected from the group consisting of: a piston, a DC motor, a stepper motor, a linear actuator, an electroactive polymer (EAP), and a pneumatic muscle.

12. The wearable robotic device of claim 8, wherein the joint is selected from the group consisting of: a hand joint, an elbow joint, a wrist joint, a shoulder joint, a sternoclavicular joint, a vertebral joint, a temporomandibular joint, a sacroiliac joint, a hip joint, a knee joint, an ankle joint, and a foot joint.

13. The wearable robotic device of claim 8, wherein the subject is a human.

14. The wearable robotic device of claim 8, wherein the subject is a canine.

15. The wearable robotic device of claim 8, wherein the wearable device is a glove.

16. The wearable robotic device of claim 15, wherein the glove includes a plurality of fingers and each finger is associated with at least one actuator.

17. The wearable robotic device of claim 8, further comprising:
one or more force sensors adapted and configured to detect movement by the subject.

18. The wearable robotic device of claim 8, further comprising:
a pair of force sensors positioned on opposite sides of a subject's bone.

* * * * *